(12) United States Patent
Lillard, Jr. et al.

(10) Patent No.: US 10,058,093 B2
(45) Date of Patent: Aug. 28, 2018

(54) NANOFORMULATIONS FOR PLANTS

(71) Applicant: JYANT TECHNOLOGIES, INC., Marietta, GA (US)

(72) Inventors: James W. Lillard, Jr., Smyrna, GA (US); Rajesh Singh, Atlanta, GA (US)

(73) Assignee: JYANT TECHNOLOGIES, INC., Marietta, GA (US)

( * ) Notice: Subject to any disclaimer, the term of this patent is extended or adjusted under 35 U.S.C. 154(b) by 32 days.

(21) Appl. No.: 15/470,215

(22) Filed: Mar. 27, 2017

(65) Prior Publication Data

US 2017/0280712 A1 Oct. 5, 2017

Related U.S. Application Data

(60) Provisional application No. 62/314,836, filed on Mar. 29, 2016.

(51) Int. Cl.

| | | |
|---|---|---|
| *A01N 63/02* | (2006.01) | |
| *A01N 25/26* | (2006.01) | |
| *A01N 43/653* | (2006.01) | |
| *A01N 43/54* | (2006.01) | |
| *C05B 17/00* | (2006.01) | |
| *C05G 3/00* | (2006.01) | |
| *A01N 37/30* | (2006.01) | |
| *A01N 25/28* | (2006.01) | |

(52) U.S. Cl.
CPC ............. *A01N 25/26* (2013.01); *A01N 25/28* (2013.01); *A01N 37/30* (2013.01); *A01N 43/54* (2013.01); *A01N 43/653* (2013.01); *A01N 63/02* (2013.01); *C05B 17/00* (2013.01); *C05G 3/0041* (2013.01)

(58) Field of Classification Search
CPC ........ A01N 63/02; A01N 63/00; A01N 63/04; A01N 37/30
See application file for complete search history.

(56) References Cited

U.S. PATENT DOCUMENTS

| | | |
|---|---|---|
| 6,511,939 B1 | 1/2003 | Burns et al. |
| 7,579,164 B2 | 8/2009 | Bender et al. |
| 2003/0013609 A1 | 1/2003 | Burns et al. |
| 2006/0014645 A1* | 1/2006 | Yavitz .................... A01N 25/28 504/241 |
| 2009/0156404 A1 | 6/2009 | Kupatt, Jr. |
| 2011/0052710 A1* | 3/2011 | Lillard ................... A61K 9/146 424/491 |

OTHER PUBLICATIONS

International Search Report, International Preliminary Report on Patentability and Written Opinion, issued in International Patent Application No. PCT/US2017/024347, dated Jun. 16, 2017.
Twizeyimana, M., et al., "Comparison of Field, Greenhouse, and Detached-Leaf Evaluations of Soybean Germplasm for Resistance to Phakopsora Pachyrhizi," Plant Disease, Sep. 2007, vol. 91, pp. 1161-1169.

* cited by examiner

*Primary Examiner* — Johann R Richter
*Assistant Examiner* — Danielle Sullivan
(74) *Attorney, Agent, or Firm* — Ping Wang; Morris, Manning & Martin, LLP

(57) ABSTRACT

The present application relates to a nanoparticle compositions and methods for targeted delivery of a bioactive agent to a plant. In one embodiment, the nanoparticle composition includes a coronatine-coated nanoparticle formulated to deliver one or more bioactive agent through plant stomata. A variety of bioactive agents may be included in the nanoparticles, including one or more bactericides, fungicides, insecticides, acaricides, miticides, nemanticides, molluscicides, herbicides, plant nutrients, fertilizers, plant growth regulators, or combinations thereof.

19 Claims, 8 Drawing Sheets

NANOFORMULATIONS FOR PLANTS

This application claims priority to U.S. Provisional Patent Application Ser. No. 62/314,836, filed Mar. 29, 2016. The entirety of the aforementioned application is incorporated herein by reference.

FIELD

This application generally relates to nanoparticle compositions and methods for improving the bioavailability of macro and micronutrients to plants and protecting against plant pathogens.

BACKGROUND

Agriculture is a multi-billion dollar industry. Fertile soils are required for improved plant growth. In their absence, fertilizers are often utilized for agricultural crops. Air and water supply three important elements for plant growth, specifically carbon (C), hydrogen (H) and oxygen (O). When chlorophyll (green pigments) in plants is exposed to light in photosynthesis, these three elements are combined to form carbohydrates and release oxygen. Water is brought into the plant by root absorption from soil. Carbon dioxide ($CO_2$) enters the plant through small leaf openings called stomata. The rate at which photosynthesis occurs is directly influenced by water and nutritional status of the plant, and is largely determined by the genetics of the plant.

Fifteen essential nutrients are supplied by soil. Of these, nitrogen (N), phosphorus (P) and potassium (K) are referred to as primary nutrients or macronutrients. This is because (1) they are required by the plant in large amounts relative to other nutrients, and (2) they are the nutrients most likely to be found in limiting supply when plant growth and development is impeded. Calcium (Ca), magnesium (Mg) and sulfur (S) are termed secondary nutrients, because their absence is less likely to constitute growth-limiting factors in soil. Zinc (Zn), chlorine (Cl), boron (B), molybdenum (Mo), copper (Cu), iron (Fe), manganese (Mn), cobalt (Co) and nickel (Ni) are termed micronutrients, because (1) they are found in only very small amounts relative to other plant nutrients in the average plant, and (2) they are least likely to be limiting plant growth and development in many soil systems Fertilizers, particularly synthetic fertilizers have a major potential to pollute soil, water and air; in recent years, many efforts were done to minimize these problems by agricultural practices and the design of the new improved fertilizers. Conventional fertilizers are generally applied on the crops by either spraying or broadcasting. However, one of the major factors that decide the mode of application is the final concentration of the fertilizers reaching to the plant. In practical scenario, very less concentration (much below to minimum desired concentration) reaches to the targeted site due to leaching of chemicals, drift, runoff, evaporation, hydrolysis by soil moisture, and photolytic and microbial degradation. It has been estimated that around 40-70% of nitrogen, 80-90% of phosphorus, and 50-90% of potassium content of applied fertilizers are lost in the environment and could not reach the plant, which causes sustainable and economic losses.

In addition, plant pathogens, account for major economic losses in the agriculture industry. Moreover, global regulatory requirements are becoming more and more demanding with respect to the use of pesticides, particularly with respect to unmanaged or unnecessary pesticide residues. Thus, there exist mutually contradictory requirements of farmers to control destructive pathogens, which demands that more pesticide be used, while increasing pressures from regulatory agencies demand that less pesticide be used. These regulatory demands are aimed to protect the safety and health of agricultural workers and the general public. It is also well-known that the general public would like less chemical residue on fruits and vegetables. A particular consequence of this situation is that there is an increasing need to have more efficient methods of protecting plants from plant pathogens, especially economically important crops, fruits and vegetables.

The control of phytopathogenic fungi is of great economic importance since fungal growth on plants or on parts of plants inhibits production of foliage, fruit or seed, and the overall quality of a cultivated crop. Because of the vast economic ramifications of fungal propagation in agricultural and horticultural cultivations, a broad spectrum of fungicidal and fungistatic products have been developed for general and specific applications.

In view of the challenges and shortcomings in the art, there is a need for safe, environmental recyclable and user friendly compositions and methods for reducing the amounts of nutrients and fertilizers and for controlling plant pathogens, that are efficient and cost effective and will treat and provide better protection against phytopathogenic organisms.

SUMMARY

One aspect of the present application relates to a nanoparticle composition for targeted delivery of a bioactive agent to a plant. In one embodiment, the nanoparticle composition includes a coronatine-coated planetary ball milled (PBM) nanoparticle comprising a nano-matrix core, a release coating layer, and at least one bioactive agent, where the nano-matrix core comprises at least one polymeric material and the release coating layer comprises polycaprolactone and polyethylene glycol, and where the nanoparticle composition is formulated to deliver the bioactive agent through plant stomata.

In some embodiments, the nanoparticle composition is characterized such that the surface log P of the PBM-NP is >0 and the polycaprolactone:PEG ratio (w/w) is greater than 2.

A variety of bioactive agents may be included in the nanoparticle composition. In some embodiments, the nanoparticle composition includes a single bioactive agent. In other embodiments, the nanoparticle composition includes a plurality of bioactive agents. In one embodiment, the nanoparticle composition includes an anti-microbial agent, such as a bactericide, fungicide or combination thereof. In a particular embodiment, the nanoparticle composition includes the fungicides strobilurin and triazole. In another embodiment, the nanoparticle composition includes one or more pesticidal agents selected from the group consisting of insecticides, acaricides, miticides, nemanticides and molluscicides. In another embodiment, the nanoparticle composition includes one or more herbicides. In another embodiment, the nanoparticle composition includes one or more plant nutrients or fertilizers. In yet another other embodiment, the nanoparticle composition includes one or more plant growth regulators, such as antiauxins, auxins, cytokinins, defoliants, ethylene inhibitors, ethylene releasers, gametocides, gibberellins, growth inhibitors, growth retardants, growth stimulators or a combination thereof. Any combination of the above-described bioactive agents may be included in a given nanoparticle or in a plurality of different nanoparticles.

In another aspect, a method for delivering a bioactive agent to a plant, includes administering to the plant a coronatine-coated planetary ball milled (PBM) nanoparticle comprising a nano-matrix core, a release coating layer, and at least one bioactive agent, where the nano-matrix core comprises at least one polymeric material and the release coating layer comprises polycaprolactone and polyethylene glycol. Bioactive agents for inclusion in the nanoparticles according to this method include bactericides, fungicides, insecticides, acaricides, miticides, nemanticides, molluscicides, herbicides, plant nutrients, fertilizers, plant growth regulators, and combinations thereof. The nanoparticles may be administered to any one of a variety of plants or agriculturally important crops, such as soybeans, wheat, corn, rice, potatoes, and sorghum.

In another aspect, a method for protecting a plant against a plant pathogen, includes administering to the plant a coronatine-coated planetary ball milled (PBM) nanoparticle according to the present application, which includes at least one anti-microbial agent or pesticide. In a particular embodiment, the plant is a soybean, the nanoparticle composition includes strobilurin and triazole and/or the nanoparticle composition is administered in an amount sufficient to prevent or reduce soybean rust.

In another aspect, a method for improving the nutritional status of a plant includes administering to the plant administering to the plant a coronatine-coated planetary ball milled (PBM) nanoparticle according to the present application, which includes at least one plant nutrient or fertilizer.

In another aspect, a method for regulating growth of a plant includes administering to the plant a coronatine-coated planetary ball milled (PBM) nanoparticle according to the present application, which includes at least one plant growth regulator, such as an antiauxin, an auxin, a cytokinin, a defoliant, an ethylene inhibitor, an ethylene releaser, a gametocide, a gibberellin, a growth inhibitor, a growth retardant, a growth stimulator or a combination thereof.

DETAILED DESCRIPTION

Figure 1:
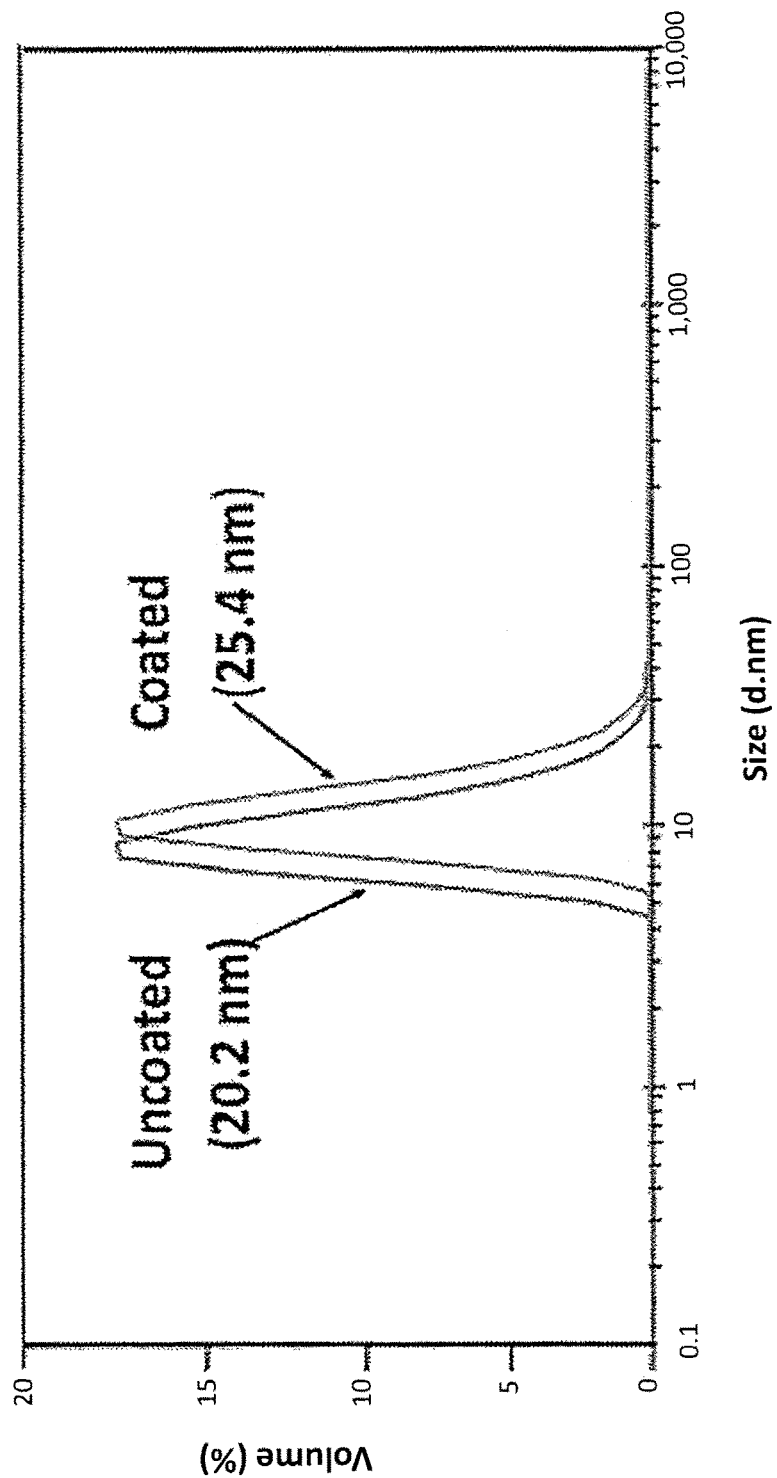
FIG. 1 shows an example of particle size distribution of fungicide encapsulated XPclad nanoparticles.
Figure 2:
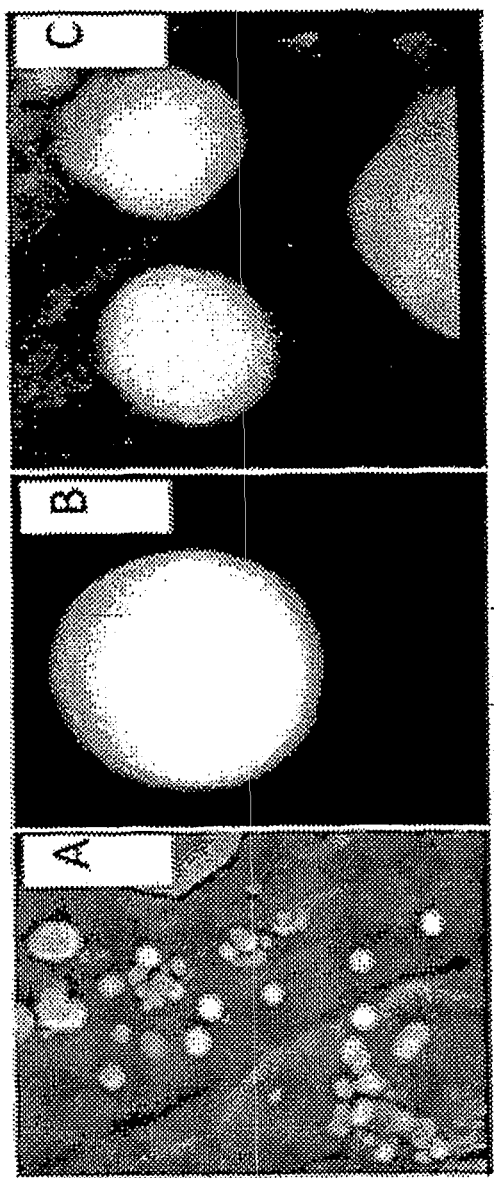
FIGS. 2A-2C show scanning electron micrographs of XPClad nanoparticles.

The following detailed description is presented to enable any person skilled in the art to make and use the invention. For purposes of explanation, specific nomenclature is set forth to provide a thorough understanding of the present application. However, it will be apparent to one skilled in the art that these specific details are not required to practice the invention. Descriptions of specific applications are provided only as representative examples. The present application is not intended to be limited to the embodiments shown, but is to be accorded the widest possible scope consistent with the principles and features disclosed herein.

Unless defined otherwise, all technical and scientific terms used herein have the same meanings as commonly understood by one of skill in the art to which the disclosed method and compositions belong. It must be noted that as used herein and in the appended claims, the singular forms "a," "an," and "the" include plural reference unless the context clearly dictates otherwise. Thus, for example, reference to "a bioactive agent" includes "one or more" bioactive agents or a "plurality" of such agents. With respect to the teachings in the present application, any issued patent, pending patent application or patent application publication described in this application is expressly incorporated by reference herein.

As used herein, the term "nanoparticle" refers to any particle having an average diameter of less than 1000 nanometers (nm). In some embodiments, nanoparticles have an average diameter of less than 300 nm, less than 100 nm, less than 50 nm, less than 25 nm, less than 10 nm or less than 5 nm. In some embodiments, each nanoparticle has a diameter of less than 300 nm, less than 100 nm, less than 50 nm, less than 25 nm, less than 10 nm or less than 5 nm.

As used herein, the terms "nanoparticle formulation" or "nanoparticle composition" are used interchangeably with reference to any substance that contains at least one nanoparticle. In some embodiments, a nanoparticle formulation is a uniform collection of nanoparticles.

As used herein, the terms "PBM nanoparticle" and "PBM-NP" are used interchangeably. PBM nanoparticles described in the present application utilize planetary ball milling to generate particles of uniform size, high loading and high transduction efficiencies in plants. This is achieved, in part, by controlling surface log P and by incorporating targeting agents and/or permeation agents as further described below. The PBM-NP composition may be formulated to penetrate the stomatal pores in plants and/or to be taken up through the soil by the root systems in plants.

As used herein, the term "XPclad nanoparticles" refers to nanoparticles formed by the planetary ball milling method. In some embodiments, PCL/PEG-coating are included in the format of XPclad nanoparticles to insure control of surface charge and targeted delivery (see e.g., patent applications: U.S. Pat. No. 8,231,907, U.S. Pat. Appl. Publ. No. 2013/0045162 and U.S. patent application Ser. No. 14/492,836).

The terms "antimicrobial" and "antimicrobial agent" refer to a substance or mixture of substances that kills or inhibits the growth of a microorganism that is pathogenic to plants or crops, such as a bacterium, fungus or virus. Exemplary antimicrobials include bactericides and fungicides, as further described below.

The terms "bactericide" and "bactericidal" refer to a substance or mixture of substances that kill or inhibit the growth of a bacterium that is pathogenic to plants or crops.

The terms "fungicide" and "fungicidal" refer to a substance or mixture of substances that kill or inhibit the growth of a fungus that is pathogenic to plants or crops.

The terms "pesticide" and "pesticidal" refer to a substance or mixture of substances that kill or inhibit the growth of a plant pest that is pathogenic to plants or crops, including insecticides, acaricides, miticides, nemanticides and molluscicides, as further described below. As used herein, the term "plant pests" refers to insects, ticks, mites, nematodes, and the like.

The terms "insecticide" and "insecticidal" refer to a substance or mixture of substances that kill or inhibit the growth of an insect that is pathogenic to plants. As used herein, the term "insects" includes all organisms in the class "Insecta" and encompasses "pre-adult" insects, which include any form of an organism prior to the adult stage, including, for example, eggs, larvae, and nymphs.

The terms "acaricide" and "acaricidal" refer to a substance or mixture of substances that kill or inhibit the growth of a member of the arachnid subclass Acari that is pathogenic to plants or crops, which includes ticks and mites.

The terms "miticide" and "miticidal" refer to a substance or mixture of substances that kill or inhibit the growth of a mite that is pathogenic to plants or crops.

The terms "nematicide" and "nematicidal" refer to a substance or mixture of substances that kill or inhibit the growth of a nematode that is pathogenic to plants or crops. The term "nematode" comprises eggs, larvae, juvenile and mature forms of nematodes.

The terms "molluscicide" and "molluscidal" refer to a substance or mixture of substances that kill or inhibit the growth of a mollusc, such as a gastropod pest (e.g., slugs and snails) that is pathogenic to plants or crops.

The terms "herbicide" and herbicidal" refer to a substance or mixture of substances that selectively kill or inhibit the growth of unwanted plants, such as weeds.

As used herein, the phrase "plant growth regulator" refers to a substance or mixture of substances which accelerate or retard the rate of growth or maturation or for otherwise altering the behavior of seeds, plants, or the produce thereof (e.g., seed germination, root growth, development processes, plant growth, maturation, and senescence, fruit set, and fruit drop) through physiological action(s). "Plant growth regulators" do not include substances or mixtures of substances substantially serving as plant nutrients, micronutrients, nutritional chemicals, plant innoculants, desiccants, biocides, pesticides, herbicides, or soil amendments.

The term "abiotic stress" refers to nonliving environmental factors, such as frost, drought, excessive heat, high winds, etc., that can have harmful effects on plants.

Stomata can serve as passive ports of plant pathogen entry. However, plants have developed defense responses to pathogen entry therethrough by closing their stomata in response to pathogen-associated molecular patterns (PAMPS). Coronatine is a non-host specific phytotoxin produced by several pathovars of the plant pathogenic bacterium *Pseudomonas syringae*, which binds the plant jasmonate (JA) receptor COR-insensitive1 (COR1). As a consequence of this binding, the stomata re-open, thereby allowing coronatine expressing bacteria to gain entry into the stomata. The present application exploits the properties of coronatine to facilitate targeted nanoparticle delivery and uptake of one or more bioactive agents through plant stomata.

Accordingly, in one aspect, the present application relates to a coronatine-coated nanoparticle for facilitating uptake of one or more bioactive agents through plant stomata. As used herein, the term "coronatine" includes coronatine and coronatine analogues, such as coronalon. Coronatine can be chemically synthesized in a laboratory or can be obtained from cultures of microorganisms that produce coronatine, either naturally or recombinantly using fermentation techniques known to those of skill in the art, including for example, batch, fed-batch, semi-batch, or continuous fermentation. For example, coronatine can be produced in vitro by *P. syringae* strain PG4180.N9 or other high coronatine-producing strains as described in U.S. Pat. Nos. 6,511,939 and 7,579,164.

The nanoparticle may be a planetary ball-milled nanoparticle (PBM-NP) or a non-PBM-NP. The bioactive agent(s) may include one or more anti-microbial agents, pesticidal agents, herbicides, plant growth regulators, or plant nutrients. In certain preferred embodiments, the nanoparticle composition is biodegradable.

In one embodiment, the nanoparticle is a coronatine-coated PBM-NP comprising a nano-matrix core, a release coating layer, and one or more bioactive agents, where the nano-matrix core comprise at least one polymeric material, where the release coating layer comprises polycaprolactone and polyethylene glycol, and where the surface log P of the PBM-NP is >0 and where the polycaprolactone:PEG ratio (w/w) is greater than 2, and where the PBM-NP is formulated to deliver the bioactive agent(s) through plant stomata.

The nanoparticle compositions of the present application can improve the efficiency of plant or crop production, reduce the impact of plant pathogens, and/or reduce abiotic stress in plants by delivering less bioactive agents while achieving the same level of protection or growth enhancement.

The release control coating facilitates delivery of the bioactive agent(s) into plant cells through the plant stomata, plant roots, or both. In addition, the release coating controls the time of release of contents, increases mechanical strength of the particles and stabilizes the bioactive agent(s) in the PBM nanoparticles. Polymers suitable for the release control coating include, but are not limited to, polycaprolactone (PCL) and PEG (or structurally/functionally analogous polymers thereof).

In one embodiment, the PBM-NPs comprise a polymeric release coating comprising PCL and PEG (or structurally/functionally analogous polymers thereof). The ratio of PCL to PEG in the polymeric release coating may vary.

In some embodiments, the PCL:PEG ratio (w/w) is less than 1:1, less than 1:2, less than 1:5, less than 1:10, less than 1:20' less than 1:50, less than 1:100, less than 1:200, less than 1:500, less than 1:1,000, less than 1:2,000, less than 1:5,000, less than 1:10,000, less than 1:20,000 or less than 1:50,000.

In some embodiments, the PCL:PEG ratio (w/w) is greater than 1:1, greater than 2:1, greater than 5:1, greater than 10:1, greater than 20:1, greater than 50:1, greater than 200:1, greater than 500:1, greater than 1,000:1, greater than 2,000:1, greater than 5,000:1, greater than 10,000:1, greater than 20,000:1 or greater than 50,000:1.

In other embodiments, the PBM-NPs comprise a polymeric release coating comprising PEG but no PCL. In yet other embodiments, the PBM-NPs comprise a polymeric release coating comprising PCL but no PEG.

In some embodiments, the nano-matrix core comprises one or more polysaccharides. Exemplary polysaccharides include, but are not limited to, acacia, alginate, carrageenan, cellulose, *ceratonia*, chitosan, compressible sugar, confectioner's sugar, dextrates, dextrin, dextrose, fructose, fumaric acid, gelatin, glucose, glyceryl behenate, guar gum, lactitol, lactose, maltodextrin, maltose, mannitol, polydextrose, polymethacrylates, pregelatinized starch, sodium starch glycolate, sorbitol, starch, sterilizable maize, sucrose, tragacanth, trehalose, xylitol and combinations thereof Exemplary celluloses include, but not limited to, ethyl cellulose, hydroxyethyl cellulose, cellulose acetate, carboxymethyl cellulose calcium, carboxymethyl cellulose sodium, methylcellulose, hydroxyethyl cellulose, hydroxypropyl cellulose, hydroxypropyl methylcellulose, phthalate, hydroxypropyl methylcellulose phthalate, microcrystalline cellulose, microcrystalline cellulose, powdered cellulose and combinations thereof.

In other embodiments, the nano-matrix core comprising a biodegradable polymer selected from the group consisting of polyethylene glycol (PEG), polyglycolic acid (PGA), polylactic acid (PLA), lactic acid-glycolic acid copolymer (PLGA), polyhydroxyalkanoates (PHA), polyhydroxybutyrate-valerate (PHBV), polyvinyl alcohol (PVA), polyethylene terephthalate (PET), polyglycolide-lactide, polycaprolactone (PCL), lactic acid-ε-caprolactone copolymer (PLCL), polydioxanone (PDO), polytrimethylene carbonate (PTMC), poly(amino acid), polydioxanone, polyoxalate, a polyanhydride, a poly(phosphoester), polyorthoester, poly (L-lactic acid), polycaprolactone, poly(lactide-co-glycolide), poly(hydroxybutyrate), poly(hydroxybutyrate-co-valerate), polydioxanone, polyorthoester, polyanhydride, poly(glycolic acid), poly(D,L-lactic acid), poly(glycolic acid-co-trimethylene carbonate), polyhydroxyalkanaates, polyphosphoester, polyphosphoester urethane, poly(amino acids), cyanoacrylates, poly(trimethylene carbonate), poly (iminocarbonate), copoly(ether-esters) (e.g., PEO/PLA), polyalkylene oxalates, polyphosphazenes. cross-linked acrylic polymers, polypropylene, polyurethane, polyurethane foams, mixtures thereof, copolymers thereof and combinations thereof.

In other embodiments, the nano-matrix core comprises a carrier selected from the group consisting of porous materials, clays, silicates and combinations thereof. Exemplary clays include attapulgite, bentonite, kaolin, perlite, talc, vermiculites, zeolites, or a mixture of any two or more thereof. Exemplary silicates include aluminum silicate, magnesium aluminum silicate, hydrous calcium silicate, colloidal silicon dioxide, magnesium aluminometasilicate, and mixtures of any two or more thereof.

In certain embodiments, the nanoparticle core matrix comprises a mixture of PEG and a polymer or polysaccharide selected from the group consisting of alginate, cellulose, collagen and starch.

In certain embodiments, bioactive agents are entrapped in the nanoparticle core matrix. In some embodiments, the bioactive agents are mixed with the biodegradable polymers and polysaccharides during formation of the matrix core. In other embodiments, the matrix core is formed first and the bioactive agent(s) are loaded at a later stage.

In some embodiments, the matrix core is formed by dissolving the biopolymer, such as alginate, cellulose, collagen and starch, in water to form an aqueous solution, adding the bioactive agent to the aqueous solution to form a biopolymer/bioactive agent mixture and, optionally, adding another polymer, such as PEG, to the biopolymer/bioactive agent mixture to form a final mixture. The final mixture is dried into pellet or tablet form and then milled using planetary ball milling under controlled temperature (<37° C.).

Planetary ball mills pulverize and mix materials ranging from soft and medium to extremely hard, brittle and fibrous materials. Minerals, ores, alloys, chemicals, glass, ceramics, plant materials, soil samples, sewage sludge, household and industrial waste and many other substances can be reduced in size simply, quickly and without loss. Planetary ball mills have been successfully used in many industrial and research sectors, particularly wherever there is high demand for purity, speed, fineness and reproducibility. The planetary ball mills produce extremely high centrifugal forces with very high pulverization energies and short grinding times.

Planetary ball billing techniques may include dry or wet milling. The size of the nanoparticles may be controlled by speed and duration of the planetary ball milling as further described below. In some embodiments, the grinding speed is in the range of 100-600 rpm, preferably 200-400 rpm.

In some embodiments, the nanoparticles have an average or mean particle diameter range of 0.1 to 5 nm, 5 to 30 nm, 30 to 80 nm, 30 to 180 nm, 180 to 1000 nm or 200 to 1000 nm. In other embodiments, the PBM-NP composition has an average or mean particle diameters in the range of 1 nm to 1000 nm, 1 nm to 600 nm, 1 nm to 500 nm, 1 nm to 400 nm, 1 nm to 300 nm, 1 nm to 200 nm, 1 nm to 150 nm, 1 nm to 120 nm, 1 nm to 100 nm, 1 nm to 75 nm, 1 nm to 50 nm, 1 nm to 25 nm, 1 nm to 20 nm, 1 nm to 15 nm, 1 nm to 10 nm or 1 nm to 5 nm or 1 nm to 2 nm. In other embodiments, the PBM-NP composition has an average or mean particle diameter of 15 nm to 200 nm, 25 nm to 200 nm, 50 nm to 200 nm, or 75 nm to 200 nm. In some embodiments, the average particle diameter is within a range of 10 nm to 300 nm, 10 nm to 200 nm, 10 nm to 100 nm, 10 nm to 50 nm, 10 nm to 25 nm. In other embodiments, the PBM-NP composition has an average or mean particle diameter between 0.1 nm to 1 μm, 0.1 to 0.5 nm or 0.1 to 0.2 nm.

In some embodiments, at least 80%, at least 85%, at least 90%, at least 95%, at least 98%, at least 99%, at least 99.5%, at least 99.9% or at least 99.99% of the particles in a nanoparticle formulation are within any of the ranges described herein. As used herein, the term "uniform", is used with reference to a nanoparticle composition in which the individual nanoparticles have a specified range of particle diameter sizes in which at least 80%, at least 85%, at least 90%, at least 95%, at least 98%, at least 99%, at least 99.5%, at least 99.9% or at least 99.99% of the particles in a nanoparticle formulation are within the above-described ranges.

In certain embodiments, the nanoparticle composition is substantially free of particles having a diameter larger than 300 nm, 250 nm, 200 nm, 150 nm, 120 nm, 100 nm, 75 nm, 50 nm, 25 nm, 15 nm, 10 nm or 5 nM. As used herein, the term "substantially free" is used with reference to a nanoparticle composition in which greater than 95%, greater than 98%, greater than 99%, greater than 99.5% or greater than 99.9% of the nanoparticles are smaller than specified diameter above.

Chemical side chains in the nanoparticle surfaces may be classified as lipophilic (hydrophobic), lipophobic (hydrophilic), or neutral. The lipophilicity of those side chains may be determined by measuring the partition coefficient of the chemical side chains in the nanoparticle between a nonpolar solvent (e.g., ethanol, dioxane, acetone, benzene, n-octanol) and water, at STP. The partition coefficient (P) is defined as the ratio of the equilibrium concentrations of a dissolved substance in a two-phase system consisting of two largely immiscible solvents. One such system is n-octanol:water; the octanol phase will contain about 20% water and the water phase about 0.008% octanol. Thus, the relevant partition coefficient (P) is the ratio of the molar concentration of the solute in octanol saturated with water to its molar concentration in water saturated with octanol. N-octanol is a useful surrogate for biological membranes because it, like many membrane components, is amphiphilic. The lipophilicity of the PBM-NP may be defined as the logarithm of the partition coefficient (log P); it will be positive for molecules which prefer the nonpolar solvent.

The PBM-NPs exemplified in FIG. 1 are expected to possess increased transduction efficiency due to the positive surface Log P (partition coefficient) value of the PBM-NP. The surface log P of the PBM-NP can be varied depending on the nature and concentration(s) of the coating layer components.

Log P values may be measured directly, or estimated approximately using mathematical algorithms. Log P values can be determined, for example by calculation using the EPI suite v3.10, 2000, U.S. Environmental Protection Agency or using software providing such estimations from Advanced Chemistry Design Inc.

In some embodiments, the Log P value of the PBM-NP is 0 or less than 0. In some embodiments, the Log P value is between 0 and -5. In some embodiments, the Log P value is between 0 and -1. In other embodiments, the Log P value is between −1 and -2. In other embodiments, the Log P value is between −2 and -3. In other embodiments, the Log P value is between −3 and −4. In other embodiments, the Log P value is between −4 and -5.

In other embodiments, the Log P value of the PBM-NP is greater than 0. In some embodiments, the Log P value is between 0 and 7. In some embodiments, the Log P value is between 0 and 2. In other embodiments, the Log P value is between 2 and 3. In other embodiments, the Log P value is between 3 and 4. In other embodiments, the Log P value is between 4 and 5. In other embodiments, the Log P value is between 5 and 6. In other embodiments, the Log P value is between 6 and 7.

Zeta potential is a measurement of the electric potential at a shear plane. A shear plane is an imaginary surface separating a thin layer of liquid bound to a solid surface (e.g., nanoparticle surface) and showing elastic behavior from the rest of liquid (e.g., liquid dispersion medium) showing normal viscous behavior. Zeta potential of substrates or surfaces can be modified by adding anions or cations. For substrates or surfaces interacting with cells and/or tissue, the zeta potential can be modified by conjugating molecules that have a net negative or positive charge. These molecules include, but are not limited to amino acids, nucleotides, vitamins, aromatic acids, polysaccharides, polymers, and polypeptides. Both negative and positively charged particles can be delivered if the Log P of the surface is amiable to delivery.

In some embodiments, the PBM-NPs have a zeta potential ranging between −80 mV and +80 mV. In other embodiments, nanoparticles have a zeta potential ranging between −50 mV and +50 mV. In some embodiments, nanoparticles have a zeta potential ranging between −25 mV and +25 mV. In other embodiments, nanoparticles have a zeta potential ranging between −10 mV and +10 mV. In some embodiments, nanoparticles have a zeta potential between −80 mV to −70 mV, between −60 mV to −50 mV, between −40 mV to −30 mV, between −25 mV to −20 mV, between −15 mV to −10 mV, or between −5 mV to 0 mV. In some embodiments, nanoparticles have a zeta potential between +5 mV to +10 mV, between +10 to +15 mV, between +15 mV to +20 mV, between +25 mV to +30 mV, between +30 mV to +35 mV, between +35 mV to +40 mV or between +45 mV to +50 mV. In other embodiments, nanoparticles have a zeta potential that is about 0 mV. In still other embodiments, nanoparticles have a zeta potential between −5 mV to −80 mV, between −5 mV to −70 mV, between −5 mV to −60 mV, between −5 mV to −50 mV, between −5 mV to −40 mV, between −5 mV to −30 mV, between −5 mV to −20 mV, between or between −5 mV to −10 mV.

In some embodiments the PBM-NP compositions are formulated as a dry powder. The dry powder may be administered to a subject directly or it may be reconstituted in a suitable solvent or carrier prior to administration.

In some embodiments the PBM-NP compositions are formulated as emulsions or dispersions. In general, an emulsion or dispersion is formed from at least two immiscible materials, one of which will constitute the dispersion medium (i.e., the liquid medium in which particles (e.g., nanoparticles), which constituted the "dispersed medium") are dispersed. An "oil-in-water" dispersion is one in which oily particles are dispersed within an aqueous dispersion medium. A "water-in-oil" dispersion is one in which aqueous particles are dispersed within an oily dispersion medium. Oil-in-water and water-in-oil dispersions are discussed in further detail below. Those of ordinary skill in the art will appreciate that a dispersion can be formed from any two immiscible media and is not limited strictly to combinations of aqueous and oily media. The term "dispersion medium" therefore applies broadly to any dispersion medium notwithstanding that it is common to refer to "aqueous" and "oily" categories. For example, emulsions or dispersions can be prepared from immiscible sets of hydrophobic/hydrophilic materials; polar/nonpolar materials, etc., regardless of whether such materials are strictly speaking "aqueous" or "oily". Also, in some embodiments, the PBM-NPs may be formulated within micellar structures as an oil-water-PBM-NP emulsion. In some embodiments, the coronatine-coated PBM-NP nanoparticles are further coated with one or more bioactive agents as described herein.

In other embodiments, the nanoparticles are coronatine-coated non-PBM-NP nanoparticles. In some embodiments, the coronatine-coated non-PBM-NP nanoparticles are further coated with one or more bioactive agents as described herein. As used herein, the term "non-PBM-NP" refers to a nanoparticle that is not made by planetary ball milling. The non-PBM-NP is a scaffold for delivery of bioactive agents, which can be made from any one of variety of inorganic and/or organic materials.

A non-PBM-NP can be made from a variety of inorganic or organic materials using materials and methodologies known to those of skill in the art. In some embodiments, the non-PBM-NP is made from any one of a variety of inorganic materials including, but not limited to, metals, semi-conductor materials or ceramics. Exemplary metal-based elements or compounds for the manufacture of non-PBM-NPs include aluminum, cadmium (e.g., cadmium selenide), chromium, cobalt, cobalt-chrome alloys, copper, gold, iron, iron oxide, lead, nickel, palladium, platinum, rhodium, ruthenium, silicon, silicon dioxide, silver, steel, tantalum, tin, tin oxide, titanium, titanium dioxide, tungsten metal oxides thereof, and alloys thereof. In certain embodiments, gold is preferred due to its well-known reactivity profiles and biological inertness. Ceramic materials include brushite, tricalcium phosphate, alumina, silica, and zirconia.

In other embodiments, the non-PBM-NP is made from any one of a variety of organic materials including carbon (diamond), as well as various polymeric materials, including those described above. Preferred polymers include polystyrene, silicone rubber, polycarbonate, polyurethanes, polypropylenes, polymethylmethacrylate, polyvinyl chloride, polyesters, polyethers, and polyethylene. Biodegradable, biopolymers (e.g., polypeptides such as BSA, polysaccharides, etc.), other biological materials (e.g., carbohydrates), and/or polymeric compounds as described above are also suitable for use in the non-PBM-NP.

The average diameter sizes and formulation characteristics for the non-PBM-NPs are the same as those set forth above with regard to the PBM-NPs.

Nanoparticles comprising the above materials and diameters can be produced from progressive nucleation in solution (e.g., by colloid reaction), or by various physical and chemical vapor deposition processes, such as sputter deposition. Alternatively, nanoparticles can be produced using tetrachloroauric acid (HAuCl$_4$) and a citrate-reducing agent, using methods known in the art. Besides sputter deposition, plasma-assisted chemical vapor deposition (PACVD) is another technique that can be used to prepare suitable nanoparticles.

Bioactive Agents

Exemplary bioactive agents include anti-microbial agents, such as bactericides and fungicides; pesticidal agents, such as insecticides, acaricides, miticides, nemanticides and molluscicides; herbicides; nutrients or fertilizers as further described below; plant growth regulators; and combinations thereof.

In certain embodiments, the bioactive agent is a bactericide. Exemplary bactericides include, but are not limited to bronopol; chlorothalonil+copper+maneb, chloropicrin; dichlorophen; fosetyl-AL; nitrapyrin; nickel dimethyldithiocarbamate; kasugamycin; octhilinone; furancarboxylic acid; oxytetracycline; probenazole; sodium hypochlorite; streptomycins; tecloftalam; and copper compounds, such as copper oxychloride, copper hydroxide and copper sulfate.

In other embodiments, the bioactive agent(s) include one or more fungicides. In a preferred embodiment, the bioactive agent(s) include strobilurin, triazole, or both. Strobilurin is known to target early stage infections, while triazole targets late stage infections. The attributes of coronatine, fungicides, and nanoparticles enhance fungicide efficacy, reduce eco-toxicity and increased crop production by protecting against phytofungal pathogens.

Other fungicides for use in the nanoparticles of the present application include aliphatic nitrogen fungicides (including, but not limited to, butylamine, cymoxanil, dodicin, dodine, guazatine, and iminoctadine); amide fungicides (including, but not limited to, benzovindiflupyr, carpropamid, chloraniformethan, cyflufenamid, diclocymet, diclocymet, dimoxystrobin, fenaminstrobin, fenoxanil, flumetover, furametpyr, isofetamid, isopyrazam, mandipropamid, metominostrobin, orysastrobin, penthiopyrad, prochloraz, quinazamid, silthiofam, and triforine); acylamino acid fungicides (including, but not limited to, benalaxyl, benalaxyl-M, furalaxyl, metalaxyl, metalaxyl-M, pefurazoate, and valifenalate); anilide fungicides (including, but not limited to, benalaxyl, benalaxyl-M, bixafen, boscalid, carboxin, fenhexamid, fluxapyroxad, isotianil, metalaxyl, metalaxyl-M, metsulfovax, ofurace, oxadixyl, oxycarboxin, penflufen, pyracarbolid, sedaxane, thifluzamide, tiadinil, and vangard); benzanilide fungicides (including, but not limited to, benodanil, flutolanil, mebenil, mepronil, salicylanilide, and tecloftalam); furanilide fungicides (including, but not limited to, fenfuram, furalaxyl, furcarbanil, and methfuroxam); sulfonanilide fungicides (including, but not limited to, flusulfamide); benzamide fungicides (including, but not limited to, benzohydroxamic acid, fluopicolide, fluopyram, tioxymid, trichlamide, zarilamid, and zoxamide); furamide fungicides (including, but not limited to, cyclafuramid and furmecyclox); phenylsulfamide fungicides (including, but not limited to, dichlofluanid and tolylfluanid); sulfonamide fungicides (including, but not limited to, amisulbrom and cyazofamid); valinamide fungicides (including, but not limited to, benthiavalicarb and iprovalicarb); antibiotic fungicides (including, but not limited to, aureofungin, blasticidin-S, cycloheximide, griseofulvin, kasugamycin, moroxydine, natamycin, polyoxins, olyoxorim, streptomycin, and validamycin); strobilurin fungicides (including, but not limited to, fluoxastrobin); methoxyacrylate strobilurin fungicides (including, but not limited to, azoxystrobin, bifujunzhi, coumoxystrobin, enoxastrobin, flufenoxystrobin, jiaxiangjunzhi, picoxystrobin, and pyraoxystrobin); methoxycarbanilate strobilurin fungicides (including, but not limited to, pyraclostrobin, pyrametostrobin, and triclopyricarb); methoxyiminoacetamide strobilurin fungicides (including, but not limited to, dimoxystrobin, fenaminstrobin, metominostrobin, and orysastrobin); methoxyiminoacetate strobilurin fungicides (including, but not limited to, kresoxim-methyl trifloxystrobin); aromatic fungicides (including, but not limited to, biphenyl chlorodinitronaphthalenes, chloroneb, chlorothalonil, cresol dicloran, fenjuntong, hexachlorobenzene, pentachlorophenol, quintozene, sodium pentachlorophenoxide, tecnazene, and trichlorotrinitrobenzenes); arsenical fungicides (including, but not limited to, asomate and urbacide); aryl phenyl ketone fungicides (including, but not limited to, metrafenone and pyriofenone); benzimidazole fungicides (including, but not limited to, albendazole, benomyl, carbendazim, chlorfenazole, cypendazole, debacarb, fuberidazole, mecarbinzid, rabenzazole, thiabendazole); benzimidazole precursor fungicides (including, but not limited to, furophanate, thiophanate, and thiophanate-methyl); benzothiazole fungicides (including, but not limited to, bentaluron, benthiavalicarb, benthiazole, chlobenthiazone, and probenazole); botanical fungicides (including, but not limited to, allicin, berberine, carvacrol, carvone, osthol, sanguinarine, and santonin); bridged diphenyl fungicides (including, but not limited to, bithionol, dichlorophen, diphenylamine, hexachlorophene, and parinol); carbamate fungicides (including, but not limited to, benthiavalicarb, furophanate, iodocarb, iprovalicarb, propamocarb, pyribencarb, thiophanate, and thiophanate-methyl tolprocarb); benzimidazolylcarbamate fungicides (including, but not limited to, albendazole, benomyl, carbendazim, cypendazole, debacarb, and mecarbinzid); carbanilate fungicides (including, but not limited to, diethofencarb, pyraclostrobin, pyrametostrobin, and triclopyricarb); imidazole fungicides (including, but not limited to, climbazole, clotrimazole, imazalil, oxpoconazole, prochloraz, and triflumizole); conazole (triazole) fungicides (including, but not limited to, azaconazole, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis hexaconazole, imibenconazole, ipconazole, metconazole, myclobutanil, penconazole, propiconazole, prothioconazole, quinconazole, simeconazole, tebuconazole, tetraconazole, triadimefon, triadimenol, triticonazole, uniconazole, and uniconazole-P); copper fungicides (including, but not limited to, acypetacs-copper, Bordeaux mixture, Burgundy mixture, Cheshunt mixture, copper acetate, copper carbonate, basic copper hydroxide, copper naphthenate, copper oleate, copper oxychloride, copper silicate, copper sulfate, copper sulfate, basic copper zinc chromate, cufraneb, cuprobam, cuprous oxide, mancopper, oxine-copper, saisentong, and thiodiazole-copper); cyanoacrylate fungicides (including, but not limited to, benzamacril and phenamacril); dicarboximide fungicides (including, but not limited to, famoxadone, and fluoroimide); dichlorophenyl dicarboximide fungicides (including, but not limited to, chlozolinate, dichlozoline, iprodione, isovaledione, myclozolin, procymidone, vinclozolin); phthalimide fungicides (including, but not limited to, captafol, captan, ditalimfos, folpet, and thiochlorfenphim); dinitrophenol fungicides (including, but not limited to, binapacryl, dinobuton, dinocap, dinocap-4, dinocap-6, meptyldinocap, dinocton, dinopenton, dinosulfon, dinoterbon, and DNOC); dithiocarbamate fungicides (including, but not limited to, amobam, asomate, azithiram, carbamorph, cufraneb, cuprobam, disulfiram, ferbam, metam, nabam, tecoram, thiram, urbacide, and ziram); cyclic dithiocarbamate fungicides (including, but not limited to, dazomet, etem, and milneb); polymeric dithiocarbamate fungicides (including, but not limited to, mancopper, mancozeb, maneb, metiram, polycarbamate, propineb, and zineb); dithiolane fungicides (including, but not limited to, isoprothiolane and saijunmao); fumigant fungicides (including, but not limited to, carbon disulfide, cyanogen, dithioether, methyl bromide, methyl iodide, sodium tetrathiocarbonate); hydrazide fungicides (including, but not limited to, benquinox and saijunmao); imidazole fungicides (including, but not limited to, cyazofamid, fenamidone, fenapanil, glyodin, iprodione, isovaledione, pefurazoate, and triazoxide); conazole (imidazole) fungicides (including, but not limited to, climbazole, clotrimazole, imazalil, oxpoconazole, prochloraz, and triflumizole); inorganic fungicides (including, but not limited to, potassium azide, potassium thiocyanate, and sodium azide); mercury fungicides (including, but not limited to, inorganic mercury fungicides (such as mercuric chloride, mercuric oxide and mercurous chloride) and organomercury fungicides (such as (3-ethoxypropyl)mercury bromide, ethylmercury acetate, ethylmercury bromide, ethylmercury chloride, ethylmercury 2,3-dihydroxypropyl, mercaptide ethylmercury, phosphate N-(ethylmercury)-p-toluenesulphonanilide, hydrargaphen 2-methoxyethylmercury chloride, methylmercury benzoate, methylmercury dicyandiamide, methylmercury pentachlorophenoxide, 8-phenylmercurioxyquinoline, phenylmercuriurea, phenylmercury acetate, phenylmercury chloride, phenylmercury derivative of pyrocatechol, phenylmercury nitrate, phenylmercury salicylate, thiomersal and tolylmercury acetate); morpholine fungicides (including, but not limited to, aldimorph, benzamorf, carbamorph, dimethomorph, dodemorph, fenpropimorph, flumorph, and tridemorph); organophosphorus fungicides (including, but not limited to, ampropylfos, ditalimfos, EBP, edifenphos, fosetyl, hexylthiofos, inezin, iprobenfos, izopamfos, kejunlin, phosdiphen, pyrazophos, tolclofos-methyl and triamiphos); organotin fungicides (including, but not limited to, decafentin, fentin, and tributyltin oxide); oxathiin fungicides (including, but not limited to, carboxin and oxycarboxin); oxazole fungicides (including, but not limited to, chlozolinate, dichlozoline, drazoxolon, famoxadone, hymexazol, metazoxolon, myclozolin, oxadixyl oxathiapiprolin, pyrisoxazole, and vinclozolin); polysulfide fungicides (including, but not limited to, barium polysulfide, calcium polysulfide, potassium polysulfide, and sodium polysulfide); pyrazole fungicides (including, but not limited to, benzovindiflupyr, bixafen, fenpyrazamine, fluxapyroxad, furametpyr, isopyrazam, oxathiapiprolin, penflufen, penthiopyrad, pyraclostrobin, pyrametostrobin, pyraoxystrobin, rabenzazole, and sedaxane); pyridine fungicides (including, but not limited to, boscalid, buthiobate, dipyrithione, fluazinam, fluopicolide, fluopyram, parinol, pyribencarb, pyridinitril, pyrifenox, pyrisoxazole, pyroxychlor, pyroxyfur, and triclopyricarb); pyrimidine fungicides (including, but not limited to, bupirimate, diflumetorim, dimethirimol, ethirimol, fenarimol, ferimzone, nuarimol, and triarimol); anilinopyrimidine fungicides (including, but not limited to, cyprodinil, mepanipyrim, and pyrimethanil); pyrrole fungicides (including, but not limited to, dimetachlone, fenpiclonil, fludioxonil, and fluoroimide); quaternary ammonium fungicides (including, but not limited to, berberine and sanguinarine); quinoline fungicides (including, but not limited to, ethoxyquin, halacrinate, 8-hydroxyquinoline sulfate, quinacetol, quinoxyfen, and tebufloquin); quinone fungicides (including, but not limited to, chloranil, dichlone, and dithianon); quinoxaline fungicides (including, but not limited to, chinomethionat, chlorquinox, and thioquinox); thiadiazole fungicides (including, but not limited to, etridiazole, saisentong, thiodiazole-copper, and zinc thiazole); thiazole fungicides (including, but not limited to, ethaboxam, isotianil, metsulfovax, octhilinone, oxathiapiprolin, thiabendazole, and thifluzamide); thiazolidine fungicides (including, but not limited to, flutianil and thiadifluor); thiocarbamate fungicides (including, but not limited to, methasulfocarb, prothiocarb); thiophene fungicides (including, but not limited to, ethaboxam, isofetamid, and silthiofam); triazine fungicides (including, but not limited to, anilazine); triazole fungicides (including, but not limited to, amisulbrom, bitertanol, fluotrimazole, huanjunzuo, triazbutil); Conazole (triazole) fungicides (including, but not limited to, azaconazole, bromuconazole, cyproconazole, diclobutrazol, difenoconazole, diniconazole, diniconazole-M, epoxiconazole, etaconazole, fenbuconazole, fluquinconazole, flusilazole, flutriafol, furconazole, furconazole-cis, hexaconazole, imibenconazole, ipconazole, metconazole, myclobutanil, penconazole, propiconazole, prothioconazole, quinconazole, tebuconazole, tetraconazole, triadimefon, triadimenol, triticonazole, uniconazole, uniconazole-P); triazolopyrimidine fungicides (including, but not limited to, ametoctradin); urea fungicides (including, but not limited to, bentaluron, pencycuron, and quinazamid); zinc fungicides (including, but not limited to, acypetacs-zinc, copper zinc chromate, cufraneb, mancozeb, metiram, polycarbamate, polyoxorim-zinc, propineb zinc, naphthenate, zinc thiazole, zinc trichlorophenoxide, zineb, and ziram); or an unclassified fungicides (including, but not limited to, acibenzolar, acypetacs, allyl alcohol, benzalkonium chloride, bethoxazin, bromothalonil, chitosan chloropicrin, DBCP, dehydroacetic acid, diclomezine, diethyl pyrocarbonate, ethylicin, enaminosulf, fenitropan, fenpropidin, formaldehyde furfural, hexachlorobutadiene, methyl isothiocyanate, nitrostyrene, nitrothal-isopropyl, OCH, pentachlorophenyl laurate, 2-phenylphenol phthalide, piperalin, propamidine, proquinazid, pyroquilon sodium, orthophenylphenoxide, spiroxamine, sultropen, thicyofen, and tricyclazole).

In some embodiments, the bioactive agent is a pesticide. Exemplary classes of pesticides include insecticides, acaricides, miticides, nemanticides, molluscicides, rodenticides. In certain embodiments, the nanoparticle composition includes a combination of one or more of the above classes of pesticides.

Exemplary insecticides and miticides include, but are not limited to, abamectin, acephate, acequinocyl, acriathrin, alanycarb, aldicarb, aldocycarb, alpha-methrin, *ambrosioides* extract, amitraz, aphidan, avermectin, azadirachtin, bendiocarb, benfuracarb, bensultap, beta-cyfluthrin, bifenazate, bifenthrin, brofenprox, bromophos, bufencarb, buprofezin, butocarboxim, butoxycarboxim, butylpyridaben, cadusafos, carbaryl, carbofuran, carbophenothion, carbosulphan, cartap, chloethocarb, chlorantraniliprole, chlorethoxyfos, chlorfenapyr, chlorfenvinphos, chlorfluazuron, chlormephos, chlorpyrifos, cis-resmethrin, clocythrin, clofentezine, cloprothrin, clothianidin, cyanophos, cyfluthrin, cyhalothrin, cyhexatin, cypermethrin, cryolite, cyromazine, delta-methrin, demeton, diafenthiuron, diazinon, 8-methrin, dichlofenthion, dichlorvos, dicliphos, dicofol, dicrotophos, diethion, diflubenzuron, dimefox, dimethoate, dimethylvinphos, dinotefuran, dioxathion, disulfoton, edifenphos, emamectin benzoate, endosulfan, esfenvalerate, ethiofencarb, ethion, ethofenprox, ethoprophos, etrimphos, fenamiphos, fenazaquin, fenbutatin oxide, fenitrothion, fenobucarb, fenothiocarb, fenoxycarb, fenpropathrin, fenpyrad, fenpyroximate, fenthion, fenvalerate, fipronil, flonicamid, fluazinam, fluazuron, flubendiamide, flucycloxuron, flucythrinate, flufenoxuron, flufenprox, fluvalinate, fonophos, formothion, fosthiazate, fubfenprox, furathiocarb, gamma-cyhalothrin, heptenophos, hexaflumuron, hexythiazox, imidacloprid, indoxacarb, insecticidal soap, iprobenfos, iron phosphate, isazophos, isofenphos, isoprocarb, isoxathion, ivermectin, kaolin, Kelthane MF, lamda-cyhalothrin, lufenuron, malathion, mecarbam, mevinphos, mesulfenphos, metaldehyde, methacrifos, methamidophos, methidathion, methiocarb, methomyl, methoxyfenozide, metolcarb, mevinphos, milbemectin, monocrotophos, morphothion, moxidectin, naled, neem oil, nitenpyram, novaluron, oils, omethoate, oxamyl, oxydemethon-m, oxydeprofos, parathion, permethrin, petroleum oil, phenthoate, phorate, phosalone, phosmet, phosphamidon, phosphamidon, phoxim, pirimicarb, pirimiphos, profenophos, promecarb, propaphos, propoxur, prothiophos, prothoate, pymetrozin, pyrachlophos, pyradaphenthion, pyresmethrin, pyrethrins, pyrethrum, pyridaben, pyrimidifen, pyriproxyfen, quinalphos, salts of fatty acids (e.g., sodium, potassium, ammonium and the like), salithion, sebufos, silaflutofen, soybean oil, spinosad, spinetoram, spiromesifen, spirotetramat, sulfotep, sulprofos, tebufenozide, tebufenpyrad, tebupirimphos, teflubenzuron, tefluthrin, temephos, terbam, terbufos, tetrachlorvinphos, thiafenox, thiamethoxam, thiodicarb, thiofanox, thiometon, thionazin, tralomethrin, triarathen, triazophos, triazuron, trichlorfon, triflumuron, trimethacarb, vamidothion, xylylcarb, zetamethrin, and combinations thereof.

In another embodiment, the bioactive agents include one or more nematicides selected from the group consisting of etridiazole, spiroxamine, fluopicolide, phosphorous acid, triadimefon+trifloxystrobin, and combinations thereof.

In another embodiment, the bioactive agents include one or more molluscicides selected from the group consisting of metal salts, such as iron(III) phosphate and aluminium sulfate, metaldehyde, methiocarb, acetylcholinesterase inhibitors, and combinations thereof.

In certain embodiments, the bioactive agent is a herbicide. Exemplary herbicides include, but are not limited to Anilides, such as Diflufenican and Propanil; Arylcarboxylic acids, such as Dichloropicolinic acid, Dicamba and Picloram; Aryloxyalkanoic acids, such as 2,4-D, 2,4-DB, 2,4-DP, Fluroxypyr, MCPA, MCPP and Triclopyr, Aryloxy-phenoxy-alkanoic esters, such as Diclofop-methyl, Fenoxaprop-ethyl, Fluazifop-butyl, Haloxyfop-methyl and Quizalofop-ethyl; Azinones, such as Chloridazon and Norflurazon; Carbamates, such as Chlorpropham, Desmedipham, Phenmedipham and Propham; Chloroacetanilides, such as Alachlor, Acetochlor. Butachlor, Metazachlor, Metolachlor, Pretilachlor and Propachlor; Dinitroanilines, such as Oryzalin, Pendimethalin and Trifluralin; Diphenyl Ethers, such as Acifluorfen, Bifenox, Fluoroglycofen, Fomesafen, Halosafen, Lactofen and Oxyfluorfen; Ureas, such as Chlortoluron, Diuron, Fluometuron, Isoproturon, Linuron and Methabenzthiazuron; Hydroxylamines, such as Alloxydim, Clethodim, Cycloxydim, Sethoxydim and Tralkoxydim; Imidazolinones, such as Imazethapyr, Imazamethabenz, Imazapyr and Imazaquin; Nitriles, such as Bromxynil, Dichlobenil and Ioxynil; Oxyacetamnides, such as Mefenacet; Sulfonylureas, such as Amidosulfuron. Bensulfuron-methyl, Chlorimuron-ethyl, Chlorsulfuron, Cinosulfuron, Metsulfuron-methyl, Nicosulfuron, Primisulfiuron, Pyrazosulfuron-ethyl. Thifensulfuron-methyl, Triasulfuron and Tribenuron-methyl; Thiolcarbamates, such as Butylate, Cycloate, Diallate, EPTC, Esprocarb, Molinate, Prosulfocarb, Thiobencarb and Triallate; Triazines, such as Atrazine, Cyanazine, Simazine, Simetryne, Terbutryne and Terbutylazin; triazinones, such as Hexazinone, Metamitron and Metribuzin; and others, such as Aminotriazole, Beefuresate, Bentazon, Cinmethylin, Clomazone, Clopyralid, Difenzoquat, Dithiopyr, Ethofumesate, Fluorochloridone, Gibberellic acid, Glufosinate, Glyphosate, Isoxaben, Pyridate, Quinchlorac, Quinmerac, Sulphosate, Tridiphane, Dalapon, Glyphosine, Ioxynil, Chlorfluorenol, Dichlorprop, Dichlofop, Mecoprop, Chlormequat, Diquat, Paraquat, Chloroacetic acid, Fluazifop, Pyridate, Chlorsulfuron, Flurenol, Sulfometuron, and natural oils.

In certain embodiments, the bioactive agent is a plant growth regulator. Exemplary plant growth regulators that can be used include antiauxins, auxins, cytokinins, defoliants, ethylene inhibitors, ethylene releasers, gametocides, gibberellins, growth inhibitors, growth retardants, growth stimulators, and unclassified growth regulators.

Exemplary antiauxins include, but are not limited to clofibric acid and 2,3,5-tri-iodobenzoic acid.

Exemplary auxins include, but are not limited to, 4-CPA, 2,4-D, 2,4-DB, 2,4-DEP, dichlorprop, fenoprop, IAA, IBA, naphthalene acetamide, α-naphthalene acetic acids, 1-naphthol, naphthoxy acetic acids, potassium naphthenate, sodium naphthenate, and 2,4,5-T.

Exemplary cytokinins include, but are not limited to, 2iP, benzyladenine, 4-hydroxyphenethyl alcohol, kinetin, and zeatin.

Exemplary defoliants include, but are not limited to, calcium cyanamide, dimethipin, endothal, ethephon, merphos, metoxuron, pentachlorophenol, thidiazuron, and tribufos.

Exemplary ethylene inhibitors include, but are not limited to, aviglycine and 1-methylcyclopropene.

Exemplary ethylene releasers include, but are not limited to, ACC, etacelasil, ethephon, and glyoxime. Exemplary gametocides include, but are not limited to, fenridazon and maleic hydrazide.

Exemplary gibberellins include, but are not limited to, gibberellins and gibberellic acid.

Exemplary growth inhibitors include, but are not limited to abscisic acid, ancymidol, butralin, carbaryl, chlorphonium, chlorpropham, dikegulac, flumetralin, fluoridamid, fosamine, glyphosine, isopyrimol, jasmonic acid, maleic hydrazide, mepiquat, piproctanyl, prohydrojasmon, propham, tiaojiean, 2,3,5-tri-iodobenzoic acid and morphactins, such as chlorfluren, chlorflurenol, dichlorflurenol and flurenol.

Exemplary growth retardants include, but are not limited to, chlormequat, daminozide, flurprimidol, mefluidide, paclobutrazol, tetcyclacis, uniconazole.

Exemplary growth stimulators include, but are not limited to, brassinolide, brassinolide-ethyl, DCPTA, forchlorfenuron, gamma-aminobutyric acid, hymexazol, prosuler, pyripropanol and triacontanol.

Exemplary signaling agents include, but are not limited to, $Ca^{2+}$, inositol phospholipids, G-proteins, cyclic nucleotides, protein kinases, protein phosphatases and sodium glutamate.

Exemplary unclassified plant growth regulators include, but are not limited to, bachmedesh, benzofluor, buminafos, carvone, choline chloride, ciobutide, clofencet, cloxyfonac, cyanamide, cyclanilide, cycloheximide, cyprosulfamide, epocholeone, ethychlozate, ethylene, fuphenthiourea, furalane, heptopargil, holosulf, inabenfide, karetazan, lead arsenate, methasulfocarb, prohexadione, pydanon, sintofen, triapenthenol and trinexapac.

In other embodiments, the nanoparticle compositions include one or more substances that may enhance defense mechanisms of the plant, including but not limited to acibenzolar-S-methyl, azadirachtin, phosphorous acid or phosphite salts, and the like.

Plant Nutrients

In another aspect, the present application relates to a nanoparticle composition where the bioactive agent is a nutrient. As used herein, the terms "plant nutrient material" or "plant nutrient" refers to any material, elements, compounds or compositions that can be used as nutrient for a plant. Examples of plant fertilizer material include, but are not limited to, nitrogen fertilizer materials, such as anhydrous ammonia, urea, ammonium nitrate, ammonium sulfate; phosphorus fertilizer materials such as diammonium phosphate, monoammonium phosphate, triple superphosphate, ordinary superphosphate, ammonium polyphosphate; potassium fertilizer materials such as potassium chloride, potassium sulfate, potassium nitrate; secondary nutrients and micronutrients such as magnesium, magnesium oxysulfate (granular), dolomitic limestone, magnesium sulfate (Epsom salts), magnesium-potassium sulfate, sulfur, K-Mag (Sul-po-mag), calcium sulfate (Gypsum), ammonium sulfate, boron, borax, solubor, calcium, calcitic limestone, bone meal, iron, iron sulfate, iron chelates, manganese, manganese oxy-sulfate, manganese chelates (soluble powder), zinc, zinc oxy-sulfate and zinc chelates.

The use of nanoparticle formulations comprising nutrients, also referred herein as "nanofertilizers" provide a means for increasing the efficiency of fertilizer delivery, reducing soil toxicity, minimizing the potential negative effects associated with over dosage, and reducing the frequency of the application. Nanofertilizers for use according to the present application can delay the release of nutrients so as to extend the period during which the fertilizer is effective. Surface coatings of nanofertilizer particles hold the material more strongly due to higher surface tension than the conventional surfaces and thus help in controlled release.

Fertilizers are often used in order to facilitate the growth of agricultural crops. Essential plant nutrients are listed in Table 1. The functions and available forms of nutrients are listed in Table 2.

TABLE 1

Essential plant nutrients and their elemental (chemical) symbol

| Nutrients Supplied by Air and Water Non-Mineral | Nutrients Supplied by the Soil System | | |
|---|---|---|---|
| | Primary or Macronutrients | Secondary | Micronutrients |
| Carbon—C | Nitrogen—N | Calcium—Ca | Zinc—Zn |
| Hydrogen—H | Phosphorus—P | Magnesium—Mg | Chlorine—Cl |
| Oxygen—O | Potassium—K | Sulfur—S | Boron—B |
| | | | Molybdenum—Mo |
| | | | Copper—Cu |
| | | | Iron—Fe |
| | | | Manganese—Mn |
| | | | Cobalt—Co |
| | | | Nickel—Ni |

TABLE 2

Functions and available forms of nutrients

| Nutrient Element | Functions in Plants | Plant Available From Soil Solution Complex | |
|---|---|---|---|
| | | Form(s) | Symbol(s) |
| Nitrogen | Promotes rapid growth, chlorophyll. formation and protein synthesis. | Anion and Cation | $NO_3-$, $NH_4+$ |
| Phosphorus | Stimulates early root growth. Hastens maturity. Stimulates blooming and aids seed formation. | Anion | $H_2PO_4-$, $HPO_4-$ |
| Potassium | Increases resistance to drought and disease. Increases stalk and straw strength. Increases quality of grain and seed. | Cation | $K+$ |
| Calcium | Improves root formation, stiffness of straw and vigor. Increases resistance to seedling diseases. | Cation | $Ca++$ |
| Magnesium | Aids chlorophyll formation and phosphorus metabolism. Helps regulate uptake of other nutrients. | Cation | $Mg++$ |
| Sulfur | Amino acids, vitamins Imparts dark green color. Stimulates seed production. | Anion | $SO_4-$ |
| Boron | Aids carbohydrate transport and cell division. | Anion | $H_3BO_3-$, $H_2BO_3-$, $HBO_3-$ |
| Copper | Enzymes, light reactions. | Cation | $Cu++$ |
| Iron | Chlorophyll formation. | Cation | $Fe++$ $Fe+++$ |
| Manganese | Oxidation-reduction reactions. Hastens germination and maturation. | Cation | $Mn++$ |
| Zinc | Auxins, enzymes. | Cation | $Zn++$ |
| Molybdenum | Aids nitrogen fixation and nitrate assimilation. | Anion | $MoO_4-$ |
| Cobalt | Essential for nitrogen fixation. | Cation | $Co++$ |
| Nickel | Grain filling, seed viability | Cation | $Ni++$ $Ni+++$ |
| Chlorine | Water use | Anion | $Cl-$ |
| Oxygen | Component of most plant compounds. | Obtained from air and water. | |
| Hydrogen | Component of most plant compounds. | | |
| Carbon | Component of most plant compounds. | | |

Exemplary nutrients/fertilizers for inclusion in the coronatine-coated nanoparticles include, but are not limited to ammonium molybdate, ammonium nitrate, ammonium nitrate sulfate, ammonium polyphosphate, ammonium sulfate, ammonium thiosulfate, anhydrous ammonia, aqua ammonia, azurite, bone meal, borax, boric acid, boron, boron frit, calcitic limestone, calcium, calcium borate, calcium carbonate, calcium chloride, calcium cyanamid, calcium nitrate, calcium oxide, calcium sulfate (Gypsum), chloride, copper chelates, copper frits, copper polyflavonoid, copper sulfate, crotonylidene diurea, cupric acetate, cupric ammonium phosphate, cupric oxide, cuprous oxide, diacyandiamide, diammonium phosphate, disodium octaborate tetrahydrate, disodium tetraborate, dolomitic limestone, ferric oxide, ferric sulfate, ferritin, ferrous ammonium phosphate, ferrous ammonium sulfate, ferrous carbonate, ferrous oxalate, ferrous oxide, ferrous sulfate, gypsum, iron, iron ammonium polyphosphate, iron chelate, iron chelates, iron fits, iron lignosulfonate, iron methoxyphenylpropane, iron polyflavonoid, iron sulfate, isobutylidene diurea, K-Mag (Sul-po-mag), lime, magnesium, magnesium ammonium phosphate, magnesium borate, magnesium nitrate, magnesium oxide, magnesium oxy-sulfate (granular), magnesium-potassium sulfate, magnesium sulfate, malachite, manganese, manganese ammonium phosphate, manganese carbonate, manganese chelates, manganese chloride, manganese fits, manganese methoxyphenyl propane, manganese oxide, manganese oxy-sulfate, manganese polyflavonoid, manganese sulfate, molybdenum fit, molybdenum sulfide, molybdenum trioxide, monoammonium phosphate, monopotassium phosphate, ordinary superphosphate, potassium carbonate, potassium chloride, potassium magnesium sulfate, potassium metaphosphate, potassium nitrate, potassium sulfate, sodium borate, sodium borosilicate, sodium molybdate, sodium nitrate, sodium tetraborate, sodium tetraborate decahydrate, sulfur, solubor, superphosphate, triple superphosphate, urea, zinc, zinc ammonium phosphate, zinc carbonate, zinc chelates, zinc fit, zinc lignosulfonate, zinc oxide, zinc oxy-sulfate, zinc phosphate, zinc polyflavonoid, zinc sulfate, zinc sulfide, and combinations thereof.

Plant Diseases for Treatment

Numerous classes of plant pathogenic fungi, including oomycetes, ascomycetes, and basidiomycetes, cause infections treatable or preventable by compositions of the present application in a plant. Agronomically important diseases caused by fungal phytopathogens include: glume and leaf blotch, late blight, stalk/head rot, rice blast, leaf blight and spot, corn smut, wilt, sheath blight, stem canker, root rot, blackleg and kernel rot. Examples of fungi that may cause infections treatable or preventable by compositions of the present application in a plant include *Cercospora beticola* (*Cercospora* leaf spot), *Mycosphaerella fifiensis* (Black sigatoka), *Glomerella cingulata* (Anthracnose) and *Cladosporium caryigenum* (pecan scab). In general, fungal plant diseases can be classified into two types: those caused by soilborne fungi and those caused by airborne fungi. Soilborne fungi cause some of the most widespread and serious plant diseases, such as root and stem rot caused by *Fusarium* spp. and root rot caused by *Phytophthora* spp. For example, *Phytophthora parasitica* var. *nicotiana*, a soilborne oomycete found, in many tobacco growing regions worldwide, causes black shank, a highly destructive root and stem rot disease of many varieties of cultivated tobacco. Since airborne fungi can be spread long distances by wind, they can cause devastating losses, particularly in crops which are grown over large regions.

A number of pathogens have caused widespread epidemics in a variety of crops. Diseases caused by airborne fungi are stem rust (*Puccinia graminis*) on wheat, corn smut (*Ustilago maydis*) on corn, and late blight disease (*Phytophthora infestans*) on potato and tomato. *Plasmopara viticola* is an airborne oomycete that causes downy mildew disease on grape vines. The blue mold fungus (*Peronospora tabacina*) has caused catastrophic losses in tobacco crops, particularly in the United States and Cuba. Most of these fungal diseases are difficult to combat, and farmers and growers must use a combination of practices, such as sanitary measures, resistant cultivars, and effective fungicide against such diseases. Billions of dollars are spent annually for chemical control of plant-pathogenic fungi. As a result, there is today a real need for new, more effective and safe means to control plant-pathogenic fungi, particularly oomycete, which are responsible for major crop loss.

Many plant pathogens and pests are extending their ranges and emerging in habitats where they had not been present before. While sporadic invasion by these species has been terminated in the past, mostly due to unfavorable weather conditions, now they more frequently survive and become endemic at a faster rate. This problem of pathogen dispersal is compounded by increased human mobility and long distance traveled by man and crop distribution. A recent example of the impact climate change has had on plant disease is the invasion of the Asian SBR fungus, *P. pachyrhizi*, into South and North America. Initially, a less aggressive relative of *P. pachyrhizi*, known as *Phakopsora meibomiae* and referred to as the Latin-American isolate, was indigenous in South America where it was not considered a major problem in soybean cultivation. This situation dramatically changed with the appearance of the Asian-Australian isolate, *P. pachyrhizi*, which is now the top ranking soybean disease.

By way of example, the nanoparticle fungicide delivery system of the present application can improve the efficiency of soybean production and reduce the impact of abiotic stress and/or plant pathogens by, e.g., *Phakopsora pachyrhizi* by delivering less fungicide while achieving the same level of protection. Using XPclad nanoparticles to deliver fungicides, 100-fold less of these agents can be applied to soybean crops, thereby improving soil and water quality. Further, using XPclad nanoparticles to deliver bioactive agents enhances crop production by reducing the impact of harmful agents (e.g., fungicides) in the environment through the utility of the engineered nanoparticles described herein.

Figure 3:
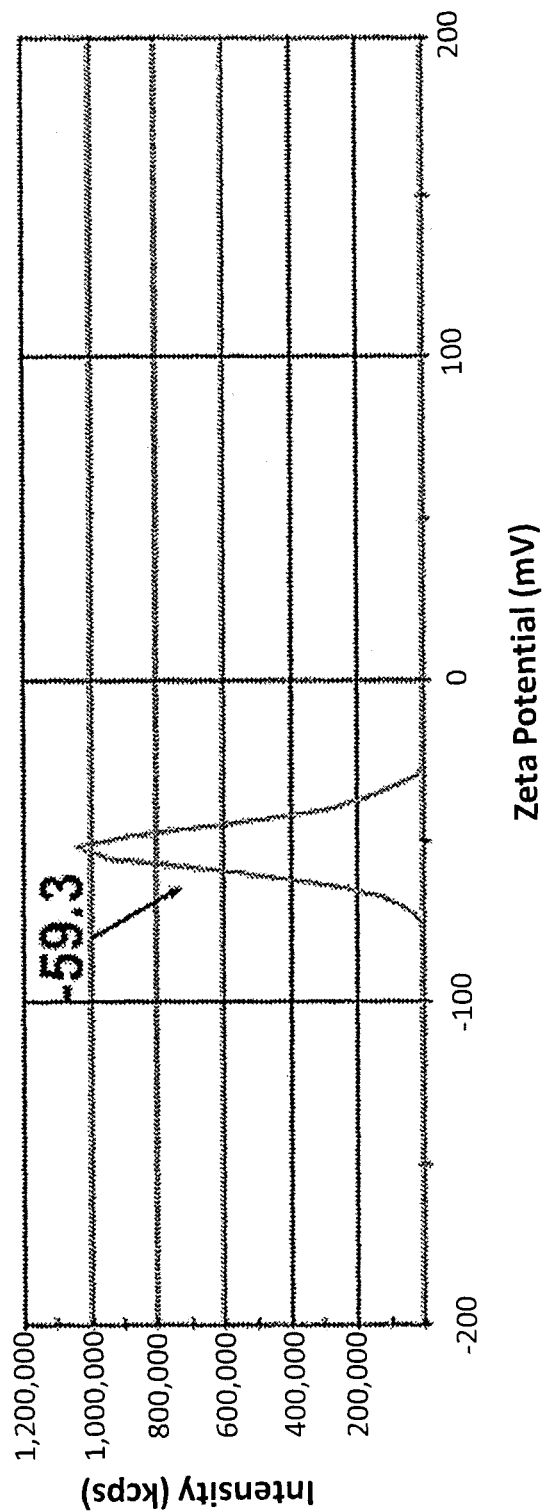
FIG. 3 shows the Zeta potential of fungicide encapsulated XPclad nanoparticles.
Figure 4:
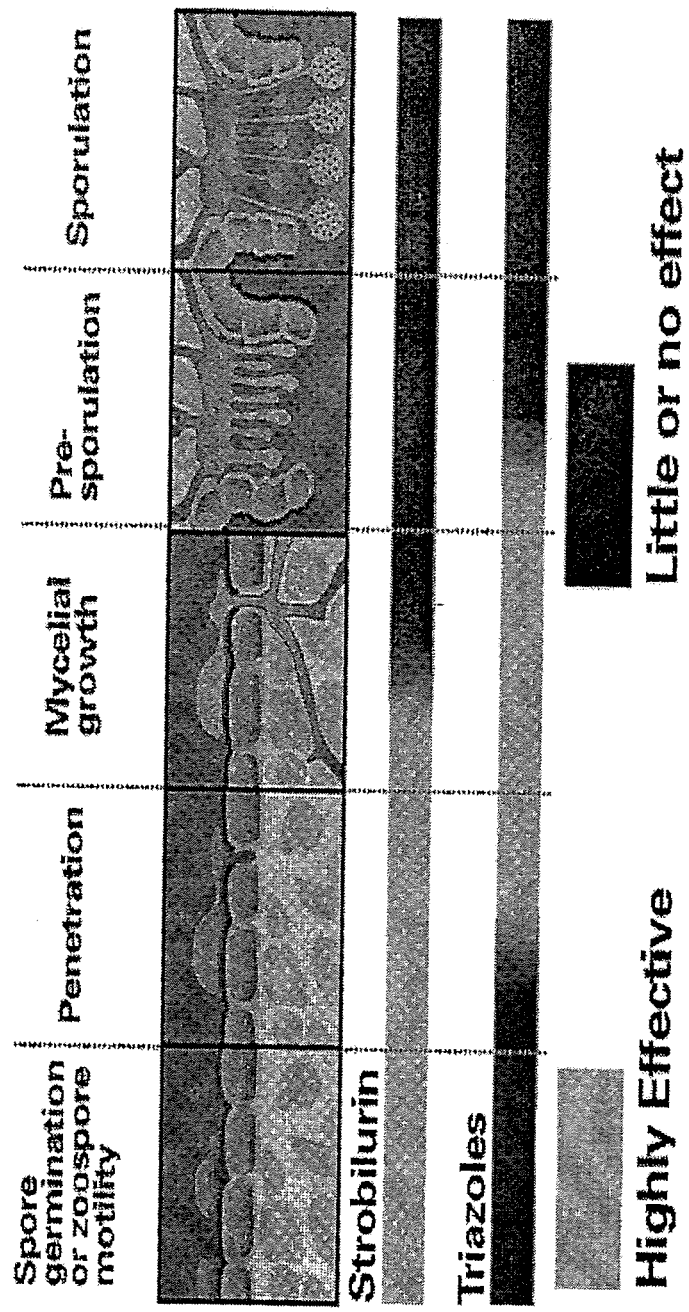
FIG. 4 is a schematic illustrating XPclad fungicide impact on soybean rust developmental stages.
Figure 5A:
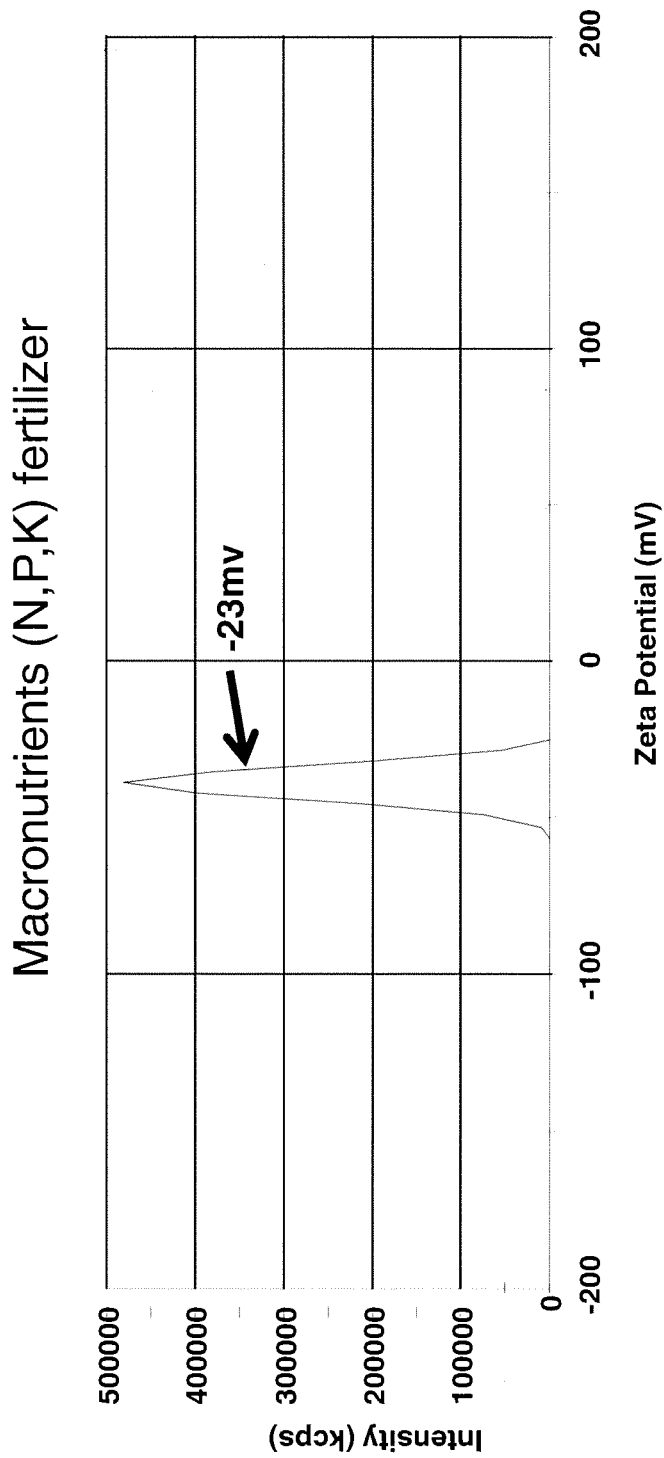
FIGS. 5A-5D show size distribution (FIGS. 5A and 5C) and zeta potential distribution (FIGS. 5B and 5D) of representative macronutrient nanofertilizers (FIGS. 5A and 5B) and micronutrient nanofertilizers (FIGS. 5C and 5D).
Figure 5B:
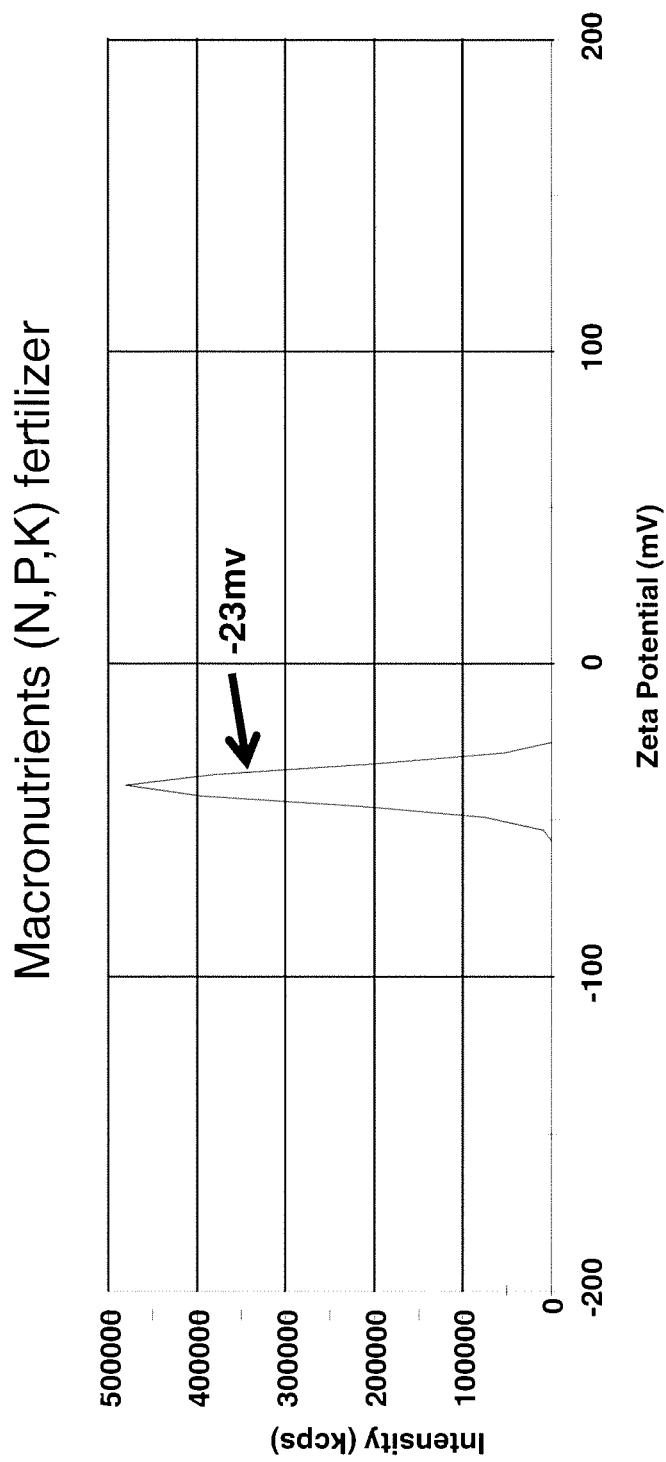
Figure 5C:
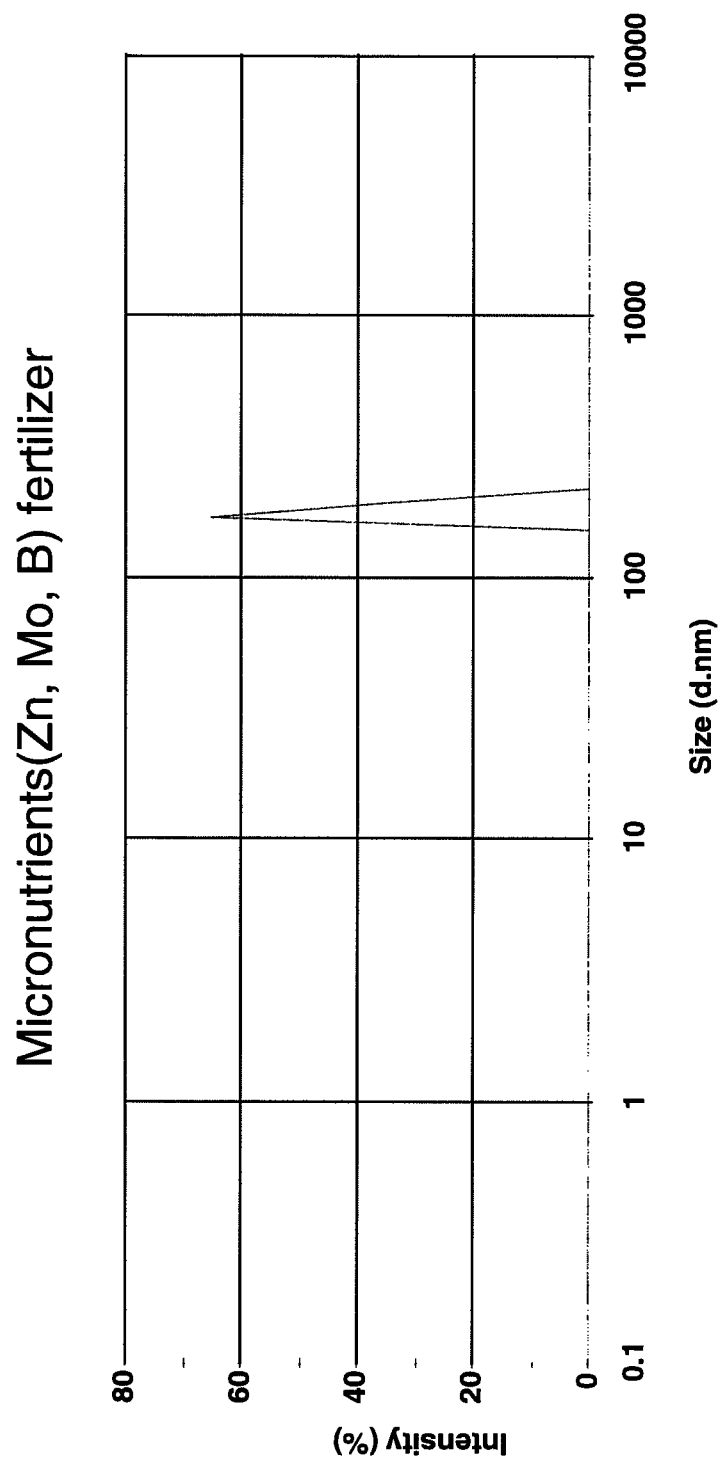
Figure 5D:
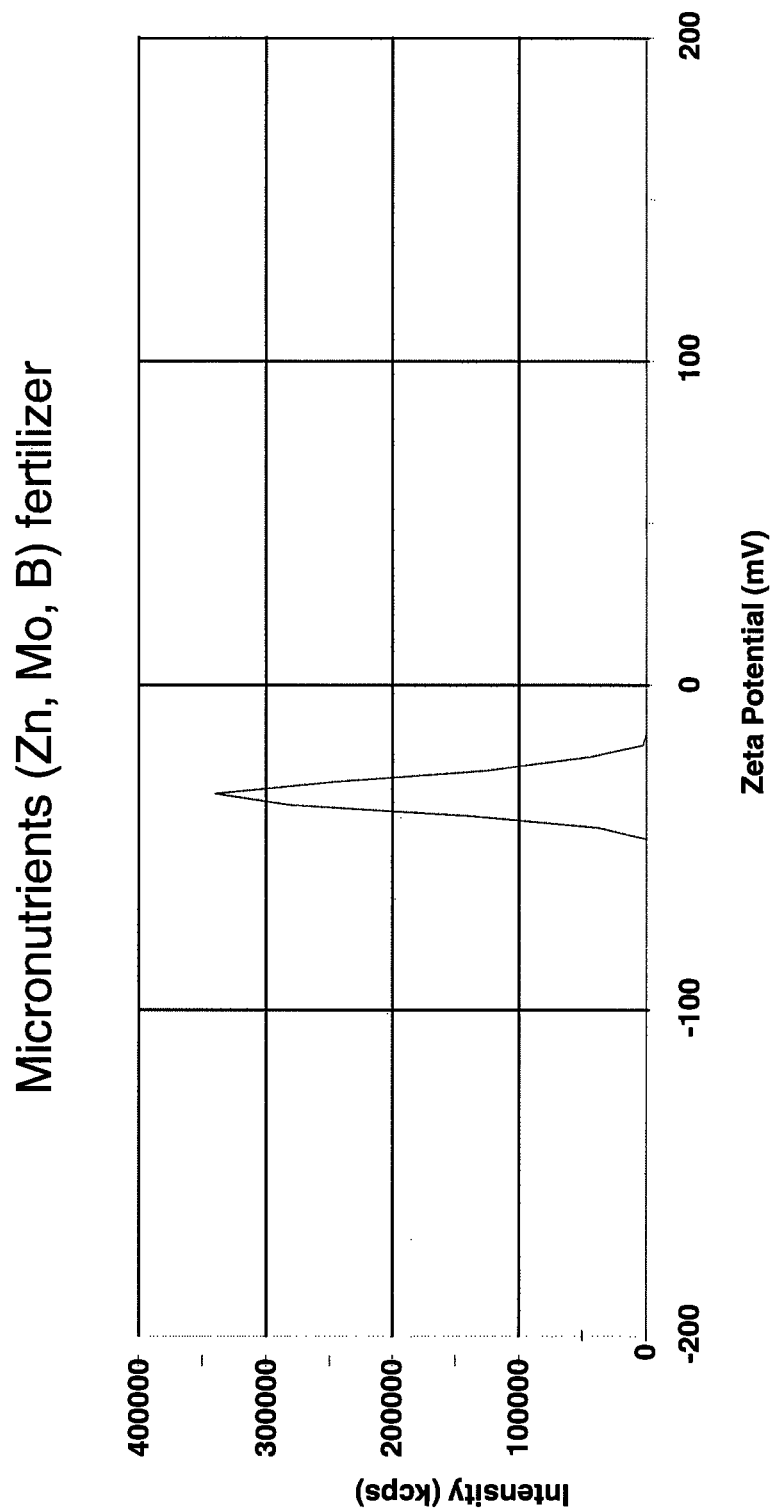

Xpclad nanoparticles have several advantages over existing nano-vehicles. The method of producing Xpclad nanoparticles is rapid (4 hours) and reproducibly (SD=5 nm; Log P=−1.1±0.3) creates ~25 nm-sized (FIG. 1 and FIGS. 2A-2C) with ~60 mV zeta potential (FIG. 3) triazole and strobilurin-loaded biodegradable nanoparticles coated with polycaprolactone-polyethylene glycol copolymers conjugated to coronatine. Triazole- and strobilurin-loaded coronatine-coated XPclad nanoparticles enter in plant stomata and slowly release the fungicides to protect soybean rust attack from the beginning of flowering (R1) through the full pod (R6) phase of growth, protecting the plant throughout the entire period of fungal growth (FIG. 4).

Plants or Crops for Treatment

Plants to be treated with the nanoparticle composition of the present application include a variety of agricultural plants or crops of which a part or all is harvested or cultivated on a commercial scale or which serve as an important source of feed, food (e.g., vegetables, fruits), fibers (e.g., cotton and linen), combustibles (e.g., wood, bioethanol, biodiesel, and biomass) or other chemical compounds. Exemplary "agricultural plants" or "agricultural crops" include, but are not limited to cereals (e.g., wheat, rye, barley, triticale, oats, sorghum, and rice); beets (e.g., sugar beets or fodder beets); leguminous plants (e.g., beans, lentils, peas, alfalfa, and soybean); oil plants (e.g., rape, oil-seed rape, canola, *juncea* (e.g., *Brassica juncea*), linseed, mustard, olive, sunflower, cocoa bean, castor oil plants, oil palms, ground nuts, and soybean); cucurbits (e.g., squash, cucumber, and melon); fiber plants (e.g., cotton, flax, hemp, and jute); vegetables (e.g., cucumbers, spinach, lettuce, asparagus, cabbages, carrots, radish, turnip, celery, chicory, endive, brussel sprouts, parsnip, cauliflower, broccoli, garlic, eggplant, pepper, pumpkin, onions, tomatoes, potatoes, sweet potatoes, cucurbits, and paprika); lauraceous plants (e.g., avocados, cinnamon, and camphor); energy and raw material plants (e.g., corn, soybean, rape, canola, sugar cane, and oil palm); tobacco; nuts (including peanuts); coffee; tea; vines (e.g., table grapes and juice grape vines); hop; stone fruit; apple; blueberry; strawberry; pear; citrus; raspberry; pineapple; sugarcane; turf, natural rubber plants, and marijuana.

Methods for Treating Plants

In one aspect, a method for delivering a bioactive agent to a plant, includes administering to the plant a coronatine-coated planetary ball milled (PBM) nanoparticle comprising a nano-matrix core, a release coating layer, and at least one bioactive agent, where the nano-matrix core comprises at least one polymeric material and the release coating layer comprises polycaprolactone and polyethylene glycol. Bioactive agents for inclusion in the nanoparticles according to this method include bactericides, fungicides, insecticides, acaricides, miticides, nemanticides, molluscicides, herbicides, plant nutrients, fertilizers, plant growth regulators, and combinations thereof. The nanoparticles may be administered to any one of a variety of plants or agriculturally important crops, such as soybeans, wheat, corn, rice, potatoes, and sorghum.

In another aspect, a method for protecting a plant against a plant pathogen, includes administering to the plant a coronatine-coated planetary ball milled (PBM) nanoparticle according to the present application, which includes at least one anti-microbial agent or pesticide. In a particular embodiment, the plant is a soybean, the nanoparticle composition includes strobilurin and triazole and/or the nanoparticle composition is administered in an amount sufficient to prevent or reduce soybean rust.

In another aspect, a method for improving the nutritional status of a plant includes administering to the plant administering to the plant a coronatine-coated planetary ball milled (PBM) nanoparticle according to the present application, which includes at least one plant nutrient or fertilizer.

In another aspect, a method for changing the growth of a plant includes administering to the plant a coronatine-coated planetary ball milled (PBM) nanoparticle according to the present application, which includes at least one plant growth regulator, such as an antiauxin, an auxin, a cytokinin, a defoliant, an ethylene inhibitor, an ethylene releaser, a gametocide, a gibberellin, a growth inhibitor, a growth retardant, a growth stimulator or a combination thereof.

The nanoparticle compositions of the present application can be applied to a variety of leaf-bearing plants and crops. Examples of plants and food crops include, but are not limited to turf grass; flowering plants, bushes, trees, a fruit-bearing plants or vegetable; a household plant; a nursery plant; a landscape plant; a plant tissue culture, or a biomass plant. For example, the plant or seed contacted is a monocot or a dicot, including but not limited to alfalfa, rice, wheat, barley, rye, cotton, sunflower, peanut, corn, potato, sweet potato, bean, pea, chicory, lettuce, endive, cabbage, brussel sprout, beet, parsnip, turnip, cauliflower, broccoli, turnip, radish, spinach, onion, garlic, eggplant, pepper, celery, carrot, squash, pumpkin, zucchini, cucumber, apple, banana, pear, melon, citrus, strawberry, grape, raspberry, pineapple, soybean, tobacco, tomato, sorghum, or sugarcane, ornamental plants, including but not limited to, *Arabidopsis thaliana, Saintpaulia, Petunia, Pelargonium, Euphorbia pulcherrima* (poinsettia), *Chrysanthemum, Dianthus caryophyllus* (carnation), and *Zinnia*.

The nanoparticle composition of the present application may be applied to the foliage of plants by methods known in the art. For example, the nanoparticle composition may be applied to foliage as a spray-dried formulation suspended in an aqueous solution. In addition, the nanoparticle composition may be formulated with a carrier to aid dilution and dispersion, where the carrier may include any one of various types of clay, such as attaclay.

A nanoparticle composition can also be applied from the ground, for example by any agricultural spray equipment, including any sprayer, either manual or automatic, that can be used to apply a nanoparticle composition to plants, such as the foliage of plants. A concentration of a nanoparticle composition applied from the ground is $10^3$-$10^{12}$ cfu ("colony forming units")/ml, $10^4$-$10^{10}$ cfu/ml, $10^5$-$10^9$ cfu/ml, or $10^6$-$10^8$ cfu/ml. A nanoparticle composition can be applied from the ground at a wide range of volume/acre of plants treated. For example, a nanoparticle composition may be applied at 10-500 gallons/acre, 10-100 gallons/acre, or 5-20 gallons/acre.

In certain embodiments, the nanoparticle composition may be applied aerially. A nanoparticle composition or an isolated nanoparticle may be sprayed from above the plants, for example from an airplane. The concentration of a nanoparticle composition may be applied-aerially at $10^3$-$10^{12}$ cfu ("colony forming units")/ml, $10^4$-$10^{10}$ cfu/ml, $10^5$-$10^9$ cfu/ml, or $10^6$-$10^8$ cfu/ml. The nanoparticle composition can be applied at a wide range of volume/acre of plants treated. For example, a nanoparticle composition may be applied at 1-100 gallons/acre, 2-50 gallons/acre, 5-10 gallons/acre, 6-8 gallons/acre, or 2-10 gallons/acre.

The present application is further illustrated by the following examples which should not be construed as limiting. The contents of all references, patents and published patent applications cited throughout this application, as well as the Figures and Tables, are incorporated herein by reference.

EXAMPLES

Example 1: XPclad Efficacy

The minimum effective dose (MED), optimal dosing schedule (ODS) and safety profile of XPclad nanoparticles are determined. The antifungal activity ($IC_{80}$) of fungicide nanoconstructs is measured and changes in soybean growth due to XPclad nanoparticles containing fungicides are quantified, compared to the use of other methods for fungicide application.

Minimum Effective Dose (MED), Optimal Dosing Schedule (ODS) and Safety Profile Measurements The MED determination and optimal schedule will be evaluated in SBR fungus after inoculum preparation and inoculation after the establishment of inoculum in culture plate for the MED, fungus will be treated every day with 0.1 µg, 0.2 µg, 0.4 µg, 0.8 µg, 1.6 µg and 3.2 µg of triazole (commercial name Tilt 250 EC/Bumper 25 EC)- and strobilurin (commercial name Bankit) alone, or similar amounts of triazole and strobilurin in XPclad nanoparticle (per cm² area), no treatment, or XPclad nanoparticles (without triazole and strobilurin). For the optimum dosing schedule, three additional schedules will be evaluated and compared to the control of three times weekly; daily (five days per week), every four days, and weekly for 4 weeks. In order to visualize the effect of this treatment fungus will be examined under an electron microscope. Breakage of hyphal tips, where new conidia form, as well as detached conidia, will also be detected and measured. Damage to the surface of the fungal hyphae will be observed.

Inoculum Preparation and Inoculation of *P. pachyrhizi*

One monospore isolate, originally collected from infected soybean leaves were used for all experiments. Urediniospores (0.5 to 2 mg) harvested from infected leaf samples were used to inoculate the abaxial surface of Williams 82 leaf pieces. Spore suspension of 100 µl ($10^3$ spores/ml of water) will be sprayed on each leaf piece using an atomizer attached to an air compressor. A single inoculated leaf piece (approximately 4 $cm^2$) will be carefully placed in a 9 cm diameter plastic petri dish with adaxial side pressed on 1% water agar amended with 6-benzyl-aminopurine at 2 mg/liter. Petri dishes containing leaf pieces will be incubated in the dark for a period of 12 h followed by a cycle of 14 and 10 h light (380 µmol $m^{-2}$ $s^{-1}$) and darkness, respectively, inside a tissue chamber (Percival Scientific, Inc.) maintained at 23° C. Prior to incubation, dishes will be placed inside zip bags (Webster Industries, Peabody, Mass.). When uredinia erupted (9 to 13 days after inoculation), urediniospores (10 to 30) from a single uredinium will be picked using a sharp sterile needle under a dissecting microscope at 20× magnification and mixed with 40 µl of sterile water. The urediniospore suspension will then be spread onto 1.5% WA medium with a sterile glass rod. Two hours later, a single germinated urediniospore will be removed using a sharp sterile needle and transferred to a drop of sterile water with 0.01% Tween 20 and placed on a new detached leaf of Williams 82 pressed on 1% WA amended with 6-benzyl-aminopurine in a petri dish. A different sharp sterile needle will be used for picking a new germinating urediniospore. All urediniospores resulting from a single uredinium that develop from the single spore will be harvested and multiplied for use as an inoculum based on the detached-leaf assay (Twizeyimana M. et al., Plant Dis 2007; 91: 1161-9).

Scanning Electron Microscopy (SEM)

A culture of *P. pachyrhizi* will be grown on MA medium plates, sprayed with 5 ml of AT solution (10 ppm), and incubated for 3 days. Specimens will be fixed in 4% glutaraldehyde for 3 hours and treated with 0.1M-cacodylate buffer for 1 hour. After washing with distilled water, the specimen will be dehydrated in a graded ethanol series up to 100%, critical point dried, and gold-coated using an ion sputter coater. Specimens will then be observed under a Hitachi S-3500N scanning electron microscope at an accelerating voltage of 10 kV.

Transmission Electron Microscopy (TEM)

Log-phased cells of *P. pachyrhizi* ($10^8$ cells) cultured in a YPD medium, will be harvested and incubated in the presence of several different amounts of XPclad nanoparticle for 24 hrs at 28° C. TEM will be used as a complementary technique to examine sections of the treated cells, using standard procedures for fixing and embedding sensitive biological samples, which are described elsewhere (6, 7).

Inhibitory Concentration ($IC_{80}$)

The minimum inhibitory concentration (MIC) of XPclad nanoparticle for *P. pachyrhizi* will be determined by the micro dilution plates inoculated with fungi that will be incubated at 35° C., and growth turbidity/optical density measured every 24 hrs by. The 80% inhibitory concentration ($IC_{80}$) has been previously defined as the lowest concentration that inhibits 80% of the growth as determined by a comparison with growth in the control wells. The growth will be assayed with a microplate reader (Bio-Tek Instruments) by monitoring absorption at 405 nm. In the current study, amphotericin B and fluconazole will be used as positive controls toward fungi. Encapsulation of triazole and strobilurin in XPclad nanoparticles increases the antifungal effect and efficacy. Specifically, 10-fold less fungicide will be required when administered in XPclad nanoparticles than compared to positive controls. Hence XPclad particle MED and ODS will be less than fungicides given without nano-formulation. SEM analysis of the fungi will provide important information. If any of the doses chosen is not enough to kill fungus, then those doses will be removed from further studies. The highest tolerated dose will be used in the subsequent experiments.

Example 2: XPclad Targeting & Environmental Stress

In pot experiments, soybean seedlings are treated with coronatine-coated XPclad nanoparticles containing strobilurin+triazole, uncoated XPclad nanoparticles, or strobilurin+triazole alone. Plant growth parameters (shoot weight, plant height, number of pods and seed weight per plant) are recorded over 3 months and after seeding with or without *P. pachyrhizi* challenge. Scanning electron microscopy and mass spectrometry (MS) are used to precisely quantify the (extracellular and intracellular) localization of XPclad nanoparticles in leaf and pods. Similarly, gas chromatography and mass spectroscopy (GC-MS) are used to determine residual fungicide present in potted soil.

Plant Material and Propagation

5B066R2 and 5B024R2 soybean seeds (Mycogen Seed Company) are sown in 12-cm-diameter pots (two plants per pot) in a soil-less mix (Sunshine Mix, LC1; Sun Gro Horticulture Inc.), fertilized at planting with slow-release pellets (Osmocote 19-6-12; 1 to 2 pellets/$cm^2$), and placed inside a growth chamber (Percival Scientific, Inc., Boone, Iowa) maintained at 20 to 24° C. and 60 to 70% RH with 12 hours of light (500 µmol $m^{-2}$ $s^{-1}$ PAR). Leaves will be harvested from plants at growth stage V2 to V3 (i.e., approximately 28 to 40 days old) and washed in three to four changes of sterile distilled water before inoculation.

Inoculation is performed on 21 day-old soybean seedlings. Inocula are prepared using freshly collected urediniospores. Spore suspensions are made using sterile distilled water containing 0.01% Tween-20 (v/v), mixed, and filtered through a 100 µm cell strainer (BD Biosciences) to remove any debris and clumps of urediniospores. Next, urediniospores is quantified using a hemocytometer and diluted to a final concentration of 40,000 per mL. Inoculation is at the rate of one milliliter of spore suspension per plant and applied with a Preval sprayer. After inoculation, plants are placed in a dew chamber in the dark at 22° C. overnight (approximately 16 h) and then moved to Conviron growth chambers where temperatures are maintained at 23° C. during the day and 20° C. at night under a 16 hours of photoperiod with a light intensity of 280 µmol $m^{-2}$ $s^{-1}$.

Pot Test for Control of SBR

Only one foliar spray of XPclad particle or fungicide solutions is sprayed with an air-powered sprayer at 78 kPa on the foliage of 28 day-old soybean plants, and 7 days before challenging with pathogen. After a few hours in the ambient atmosphere for drying the foliar surfaces, the plants are maintained in a growth chamber. Soybean plants are inoculated with *P. pachyrhizi*. After 28 days, the disease index (on a scale of 0 to 4) on each plant is recorded and the mean value is calculated as the disease severity. Severity of SBR is rated on a scale from 0=healthy, 1=25% rust, 2=50% rust, 3=75% rust, to 4=100% rust.

Observations Recorded after XP Nanoparticle Treatment

Observations are recorded at 45 days after sowing (DAS) and also at the time of harvest. The plants are carefully removed along with intact root system from pot and observations on root traits are recorded. The root and shoot are separated, shade dried and shoots dry and root dry weights are recorded. Other observation at 45 DAS as follows 1. Plant height (cm): Plant heights are measured from the ground level to tip of the main stem and expressed in cm.
2. Root length (cm): The root length are measured from collar region to the tip of taproot and expressed in cm.
3. Lengthiest lateral root length (LLRL): Among the lateral roots, the lengthiest lateral root is measured and expressed in cm.
4. Root dry weight (g): Root dry weight signifies the amount of dry weight that is put fourth by the plant in different treatments and is recorded in grams.
5. Shoot dry weight (g): Shoot dry weight signifies the amount of dry weight in gram that is put forth by the plant in different treatments and is recorded in grams.
6. Leaf area (cm$^2$): After 45 DAS, the separated shoot is dried (not fully dried), leaves will be taken to measure the leaf area by using instrument called CID leaf area meter and is expressed in cm$^2$.
7. Root surface area (mm$^2$): After 45 DAS, the separated root portion is taken to measure the root surface area by using and it expressed in mm$^2$.
8. Root to shoot ratio: The ratio of root to shoot dry weight is calculated by dividing root dry weight with shoot dry weight.

Observations at the time of harvesting:
1. Number of pods per plant: Total number of pods per plant are recorded by counting the number of pods per plant.
2. Pod length (cm): The pod length of two pods per plant are measured and expressed as average in cm.
3. Number of seeds per pod: The number of seeds per pod is recorded.
4. Shoot dry weight (g): Shoot weight after 12 hours of drying is recorded at the time of harvesting and expressed in gram.
5. Seed yield per plant: The seed weight from each pot is expressed in grams (g) as seed yield per plant.
6. Seed index: Is defined as the weight of 25 seeds per gram.
7. Harvest index: Is defined as the ratio of seed yield to the biological yield per plant. HI=Seed yield/plant (g)/Total biological yield/plant (g).

A culture of *P. pachyrhizi* is grown on MA medium plates, sprayed with 5 ml of AT solution (10 ppm), and incubated for 3 days. This specimen is fixed in 4% glutaraldehyde for 3 hours and treated with 0.1M-cacodylate buffer for 1 hour. After washing with distilled water, the specimen is dehydrated in a graded ethanol series up to 100%, critical point dried, and gold-coated using an ion sputter coater. The specimen is observed under a Hitachi S-3500N scanning electron microscope at an accelerating voltage of 10 kV.

GC/GC-MS Analysis of the Effective Plant Extracts

To detect the fungicide content in the plant the effective plant extracts of soybean are analyzed through gas chromatography and mass spectroscopy (GC-MS) Varian model, 450 equipped with a flame ionization detector and quantization was carried out by the area normalization method neglecting response factors. The analysis is carried out using a VF-5MS capillary column (30 m×0.25 mm; 0.25 μm film thickness). The operating conditions are as follows: injection and detector temperature, 250 and 300° C. respectively; split ratio, 1:50; carrier gas, Helium with flow rate (1.0 ml/min). Oven temperature program is 50 to 300° C. at the rate of 7° C./min. Mass spectrometer conditions are: ionization potential, 70 eV; mass range from m/z, 40 to 400 amu; electron multiplier energy, 2000 V. The components of plant extracts are identified by comparison of their relative retention times and the mass spectra with those authentic reference compound and by computer matching of their MS spectra with Wiley and Nist 8 mass spectral library. The efficacy of the XPclad nanoparticle and free strobilurin+triazole is determined, based on their ability to inhibit the fungal growth. Plants receiving coronatine-coated XPclad nanoparticle containing strobilurin+triazole lead to the prevention of SBR infection without eco-toxicities, demonstrating the utility of coronatine-coated XPclad nanoparticles for the targeted delivery of fungicides with increased fungicidal efficacy.

Example 3: Nanofertilizers

Nanofertilizer formulations containing macronutrients (N, P, K) or micronutrients (Zn, Mo, B) were prepared. The size and zeta potential distribution of the nanofertilizers are shown in FIGS. 5A-5D. The Log P value of the Nanofertilizers are shown in Table 3.

TABLE 3

| Nano-fertilizer | Log P Value |
|---|---|
| Macronutrients | |
| Nitrogen (N) | −1.44 |
| Phosphorous (P) | −0.98 |
| Potassium (K) | −0.86 |
| Micronutrients | |
| Zinc (Zn) | −1.10 |
| Molybdenum(Mo) | −1.14 |
| Boron (B) | −1.15 |

Further experiments will show that both coated and uncoated nanofertilizer formulations provided good delivery of macronutrients and micronutrients in a number of test settings. In some embodiments, the nanofertilizer comprises at least 15% (w/w) N-containing, P-containing and K-containing compounds, and at least 8% (w/w) amino acids. In some embodiments, the nanofertilizer further comprises at least $10^{12}$ beneficial bacteria per unit.

The above description is for the purpose of teaching the person of ordinary skill in the art how to practice the present application, and it is not intended to detail all those obvious modifications and variations of it which will become apparent to the skilled worker upon reading the description. It is intended, however, that all such obvious modifications and variations be included within the scope of the present application, which is defined by the following claims. The claims are intended to cover the claimed components and steps in any sequence which is effective to meet the objectives there intended, unless the context specifically indicates the contrary.

What is claimed is:

1. A nanoparticle composition, comprising:
   a coronatine-coated planetary ball milled (PBM) nanoparticle comprising a nano-matrix core, a release coating layer, and at least one bioactive agent,
   wherein the nano-matrix core comprises at least one polymeric material and the release coating layer comprises polycaprolactone and polyethylene glycol, and
   wherein the nanoparticle composition is formulated to deliver the bioactive agent through plant stomata.

2. The nanoparticle composition of claim 1, wherein the surface log P of the PBM-NP is >0 and where the polycaprolactone:PEG ratio (w/w) is greater than 2.

3. The nanoparticle composition of claim 1, wherein the at least one bioactive agent is an anti-microbial agent.

4. The nanoparticle composition of claim 1, wherein the at least one bioactive agent is a fungicide.

5. The nanoparticle composition of claim 1, wherein the at least one bioactive agent comprises strobilurin and triazole.

6. The nanoparticle composition of claim 1, wherein the at least one bioactive agent comprises a pesticidal agent selected from the group consisting of insecticides, acaricides, miticides, nemanticides and molluscicides.

7. The nanoparticle composition of claim 1, wherein the at least one bioactive agent comprises a herbicide.

8. The nanoparticle composition of claim 1, wherein the at least one bioactive agent comprises a plant nutrient or fertilizer.

9. The nanoparticle composition of claim 1, wherein the at least one bioactive agent comprises a plant growth regulator.

10. A method for delivering a bioactive agent to a plant, comprising:
    administering to the plant a coronatine-coated planetary ball milled (PBM) nanoparticle comprising a nano-matrix core, a release coating layer, and at least one bioactive agent,
    wherein the nano-matrix core comprises at least one polymeric material and the release coating layer comprises polycaprolactone and polyethylene glycol.

11. The method of claim 10, wherein the at least one bioactive agent is selected from the group consisting of bactericides, fungicides, insecticides, acaricides, miticides, nemanticides, molluscicides, herbicides, plant nutrients, fertilizers, plant growth regulators, and combinations thereof.

12. The method of claim 10, wherein the plant is selected from the group consisting of soybean, wheat, corn, rice, potatoes, and sorghum.

13. A method for protecting a plant against a plant pathogen, comprising:
    administering to the plant a coronatine-coated planetary ball milled (PBM) nanoparticle comprising a nano-matrix core, a release coating layer, and at least one plant nutrient,
    wherein the nano-matrix core comprises at least one polymeric material and the release coating layer comprises polycaprolactone and polyethylene glycol, and at least one anti-microbial agent or pesticide,
    wherein the nanoparticle composition is formulated to deliver the anti-microbial agent or pesticide through stomata in the plant.

14. The method of claim 13, wherein the plant is selected from the group consisting of soybean, wheat, corn, rice, potatoes, and sorghum.

15. The method of claim 13, wherein the plant is a soybean and wherein the nanoparticle composition is administered in an amount sufficient to prevent or reduce soybean rust.

16. The method of claim 15, wherein the at least one anti-microbial agent or pesticide comprises strobilurin and triazole.

17. A method for improving the nutritional status of a plant, comprising:
    administering to the plant a coronatine-coated planetary ball milled (PBM) nanoparticle comprising a nano-matrix core, a release coating layer, and at least one plant nutrient,
    wherein the nano-matrix core comprises at least one polymeric material and the release coating layer comprises polycaprolactone and polyethylene glycol, and at least one plant nutrient or fertilizer.

18. A method for regulating growth of a plant, comprising:
    administering to the plant a coronatine-coated planetary ball milled (PBM) nanoparticle comprising a nano-matrix core, a release coating layer, and at least one plant growth regulator,
    wherein the nano-matrix core comprises at least one polymeric material and the release coating layer comprises polycaprolactone and polyethylene glycol.

19. The method of claim 18, wherein the plant growth regulator is selected from the group consisting of antiauxins, auxins, cytokinins, defoliants, ethylene inhibitors, ethylene releasers, gametocides, gibberellins, growth inhibitors, growth retardants, and growth stimulators.

* * * * *